United States Patent
Potyrailo et al.

(10) Patent No.: US 6,686,201 B2
(45) Date of Patent: *Feb. 3, 2004

(54) CHEMICALLY-RESISTANT SENSOR DEVICES, AND SYSTEMS AND METHODS FOR USING SAME

(75) Inventors: Radislav Alexandrovich Potyrailo, Niskayuna, NY (US); Joseph Richard Wetzel, Latham, NY (US)

(73) Assignee: General Electric Company, Niskayuna, NY (US)

( * ) Notice: Subject to any disclaimer, the term of this patent is extended or adjusted under 35 U.S.C. 154(b) by 72 days.

This patent is subject to a terminal disclaimer.

(21) Appl. No.: 09/681,435

(22) Filed: Apr. 4, 2001

(65) Prior Publication Data

US 2002/0173040 A1 Nov. 21, 2002

(51) Int. Cl.$^7$ .............................................. G01N 21/164
(52) U.S. Cl. ............................. 436/2; 436/5; 436/172; 422/82.08
(58) Field of Search ............................. 436/2, 5, 172; 422/82.08, 82.11

(56) References Cited

U.S. PATENT DOCUMENTS

| | | |
|---|---|---|
| 4,673,299 A | 6/1987 | Dakin |
| 5,043,285 A * | 8/1991 | Surgi ..................... 250/458.1 |
| 5,106,938 A | 4/1992 | Bookbinder et al. |
| 5,233,194 A | 8/1993 | Mauze et al. |
| 5,237,631 A | 8/1993 | Gavish et al. |
| 5,242,835 A * | 9/1993 | Jensen ..................... 250/458.1 |
| 5,356,668 A | 10/1994 | Paton et al. |
| 5,451,632 A | 9/1995 | Okumura et al. |
| 5,488,086 A | 1/1996 | Umeda et al. |
| 5,519,096 A | 5/1996 | Hara |
| 5,528,040 A | 6/1996 | Lehmann |
| 5,644,017 A | 7/1997 | Drumright et al. |
| 5,674,943 A | 10/1997 | Farah et al. |
| 5,708,957 A | 1/1998 | Chuang et al. |
| 5,717,056 A | 2/1998 | Varadarajan et al. |
| 5,744,794 A | 4/1998 | Michie et al. |
| 5,919,526 A | 7/1999 | Eckberg et al. |
| 5,919,886 A | 7/1999 | Matsuda et al. |
| 5,969,066 A | 10/1999 | Enokida et al. |
| 5,973,068 A | 10/1999 | Yamaya et al. |

(List continued on next page.)

FOREIGN PATENT DOCUMENTS

WO  WO 00/36410  6/2000

OTHER PUBLICATIONS

Raharbi, Y.; Yekta, A.; Winnik, M.A., "A Method for Measuring Oxygen Diffusion and Oxygen Permeation in Polymer Films Based on Fluorescence Quenching", *Anal. Chem.* 1999, 71, 5045–5053.

Lowry, J.H.; Mendlowitz, J.S.; Subramanian, N.S., "Optical Characteristics of Teflon AF Fluoroplastic Materials", *Opt. Eng.* 1992, 31, 1982–1985.

(List continued on next page.)

*Primary Examiner*—Jeffrey Snay
(74) *Attorney, Agent, or Firm*—Andrew J. Caruso; Patrick K. Patnode

(57) ABSTRACT

A sensor device is disclosed, as well as methods and systems for determining a barrier property of each coating of an array of barrier coatings deposited onto a fluid-permeable or fluid-impermeable substrate. The systems and methods include the sensor device having a sensing layer responsive to a fluid of interest for which the barrier property of the array of coatings are desired to be determined. The sensor device further includes an overlayer disposed between the array of barrier coatings and the sensing layer. The overlayer protects the sensing layer from being damaged by the coatings.

36 Claims, 17 Drawing Sheets

U.S. PATENT DOCUMENTS

| | | | |
|---|---|---|---|
| 5,973,126 A | 10/1999 | Ueno et al. | |
| 5,981,008 A | 11/1999 | Hofmann | |
| 5,981,073 A | 11/1999 | Pickett et al. | |
| 5,990,188 A | 11/1999 | Patel et al. | |
| 6,010,616 A | 1/2000 | Lewis et al. | |
| 6,020,207 A * | 2/2000 | Liu | 422/82.08 |
| 6,034,775 A | 3/2000 | McFarland et al. | |
| 6,087,181 A | 7/2000 | Cong | |
| 6,093,308 A | 7/2000 | Lewis et al. | |
| 6,151,123 A | 11/2000 | Nielsen | |
| 6,157,449 A | 12/2000 | Hajduk | |
| 6,182,499 B1 | 2/2001 | McFarland et al. | |
| 6,300,638 B1 * | 10/2001 | Groger et al. | 250/458.1 |
| 6,383,815 B1 * | 5/2002 | Potyrailo | 422/82.08 |

OTHER PUBLICATIONS

Buck, W.H.; Resnick, P.R.; "Properties of Amorphous Fluoropolymer Based on 2,2-Bistrifluoromethyl-4,5-Difluoro-1,3-Dioxole", $183^{rd}$ Meeting of the Electrochemical Society, 1993.

Mills, A.; Lepre, A., "Controlling the Response Characteristics of Luminescent Porphyrin Plastic Film Sensors for Oxygen", Anal. Chem. 1997, 69, 4653–4659.

Lee, S.K.; Okura, I. "Photoluminescent Determination of Oxygen Using MetalloporphyrinPolymer Sensing Systems", Spectrochim. Acta 1998, 54A, 91–100.

Amao, Y.; Asai, K.; Miyashita T.; Okura, I., "Novel Optical Oxygen Pressure Sensing Materials: Platinum Porphyrin–Styrene–Trifluoroethylmethacrylate Copolymer Film", Chem. Lett. 1999, 1031–1032.

Prince, Barry J.; Schwabacher, Alan W.; Geissinger, Peter, "A Readout Scheme Providing High Spatial Resolution for Distributed Flourescent Sensors on Optical Fibers",Anal. Chem., 2000, p. Est:8.4 (A–I).

Dakin, J.P., "Distributed Optical Fiber Sensors", Proc. SPIE–Int. Soc. Opt. Eng., 1797, (1992), 76–108.

Potyrailo, R.A.; Hieftje, G.M., "Optical Time-of-Flight Chemical Detection: Spatially Resolved Analyte Mapping with Extended–Length Continuous Chemically Modified Optical Fibers",Anal. Chem., 1998, 70, 1453–1461.

Potyrailo, R.A.; Hieftje, G.M., "Optical Time–of–Flight Chemical Detection: Absorption–Modulated Fluorescence for Spatially Resolved Analyte Mapping in a Bidirectional Distributed Fiber–Optic Sensor" Anal. Chem. 1998, 70, 3407–3412.

Potyrailo, R.A.; Hieftje, G.M., "Spatially Resolved Analyte Mapping with Time–of–Flight Optical Sensors", Trends Anal. Chem., 1998, 17, 593–604.

Van Dover, R.B.; Schneemeyer, L.F.; Fleming, R.M., "Discovery of a Useful Thin–Film Dielectric Using a Composition–Spread Approach", Nature, vol. 392, 1998, pp. 162–164.

Hanak, J.J., "The 'Multiple–Sample Concept' in Materials Research: Synthesis, Compositional Analysis and Testing of Entire Multicomponent Systems",Journal of Materials Science, 1970, pp. 964–971.

Ward, Michael D.; Buttry, Daniel A., "In Situ Interfacial Mass Detection with Piezoelectric Transducers", Science, vol. 249, 1990, pp. 1000–1007.

Hierlemann, A.; Ricco, A.J.; Bodenhöfer, K.; Göpel, W., "Effective Use of Molecular Recognition in Gas Sensing: Results From Acoustic Wave and in Situ FT–IR Measurements", Anal. Chem., 1999, 71, pp. 3022–3035.

Thomas, R.C.; Hierlemann, A.; Staton, A.W.; Hill, M.; Ricco, A.J., "Reflectance Infrared Spectroscopy on Operating Surface Acoustic Wave Chemical Sensors During Exposure to Gas–Phase Analytes", Anal. Chem., 1999,71, pp. 3615–3621.

Furuki, M; Lyong, S.P., "Hybrid Gas Detector of Squarylium Dye Langmuir–Blodgett Film Deposited on a Quartz Oscillator", Thin Solid Films, 1992, pp. 471–473.

Furiki, M.; Lyong, S.P., "Gas Detection by a Multi–Hybrid Sensor with Dye Langmuir–Blodgett Films Deposited on a Quartz Oscillator", Mol. Cryst. Liq. Cryst., 1993, 227, pp. 325–337.

* cited by examiner

CHEMICALLY-RESISTANT SENSOR DEVICES, AND SYSTEMS AND METHODS FOR USING SAME

FEDERAL RESEARCH STATEMENT

The U.S. Government may have certain rights in this invention pursuant to NIST contract number 70NANB9H3038.

BACKGROUND OF INVENTION

This invention relates to real-time measurements of transport of different fluids into one or more barrier coatings, and more specifically, to a sensor device having a protective overlayer, and systems and methods of using same.

Barrier coatings, such as polymers, are used for many applications, such as for packaging and for providing a protective layer on another coating. As barriers, these materials typically separate a system, such as an electronic component, a part of an engineering structure, or an article of food, from an environment. Often, such coatings are applied from liquid coating formulations. To adjust viscosity of the formulations, a wide variety of organic solvents are used. These solvents may be problematic, however, when screening new coating formulations using sensor devices.

For example, in the combinatorial discovery of coating materials for application as barrier coatings, rapid evaluation of a barrier property such as permeability of the coatings is of primary importance. The plurality of combinatorial coatings may be applied to a sensor responsive to a particular analyte, or material of interest, for which the barrier properties of the array of coatings is measured. The material of the sensing layer of these sensors, however, is often altered or dissolved by any solvent that may be present in the coating. Thus, screening of such coatings results in inaccurate results, delaying the combinatorial discovery process.

There remains an unmet need for the speedy and accurate evaluation of minute samples of barrier coating compositions, especially those compositions including solvents. There is a further need for sensing materials, devices, and methods that are not affected by common organic solvents used in barrier coatings. There is yet a further need for methods of use in conjunction with such materials and devices that provide the capability to map spatial variations of a barrier property, such as permeability, across a single barrier coating or an array of coatings.

SUMMARY OF INVENTION

The present invention discloses methods and devices for measurement of properties of materials of interest, such as permeability of barrier coatings. These measurements are accomplished using, for example, a solvent-resistant polymeric material to determine oxygen barrier properties of liquid-deposited coating arrays. In one embodiment, the oxygen-permeability measurement method disclosed provides the capability to map spatial variations of permeability across a single barrier coating or an array of coatings. In this embodiment, a fluorophore that exhibits fluorescent quenching upon exposure to molecular oxygen is incorporated in a solvent resistant sensor structure. An array of barrier coatings is applied onto the sensor. Upon exposure of the coating array to oxygen, the coating permeability is determined by the time-dependent change in the luminescence signature of the immobilized fluorophore under the barrier coating. This luminescence signal is then compared to the signal produced from a reference spatial region containing a bare sensor or a reference coating material.

To achieve the stated and other advantages of the present invention, as embodied and described below, the invention includes a device for luminescence mapping of barrier coatings, the device comprising: a luminescence sensor having at least one external surface; a chemically sensitive overlayer applied to at least one of the at least one external surface; an array of barrier coatings in a library deposited onto the chemically sensitive overlayer; a material of interest for exposure to the array of barrier coatings; and a measurement device for measuring variation in luminescence for the array of barrier coatings exposed to the material of interest.

To achieve the stated and other advantages of the present invention, as embodied and described below, the invention includes a method for measuring barrier properties of barrier coatings, the method comprising: providing a luminescence sensor having at least one external surface; applying a chemically sensitive overlayer to the at least one external surface of the luminescence sensor; placing an array of barrier coatings on the chemically sensitive overlayer; exposing the array of barrier coatings to an exposure material of interest; and measuring variation in luminescence of the array of barrier coatings.

Additional advantages and novel features of the invention will be set forth in part in the description that follows, and in part will become more apparent to those skilled in the art upon examination of the following or upon learning by practice of the invention.

DETAILED DESCRIPTION

Figure 1:
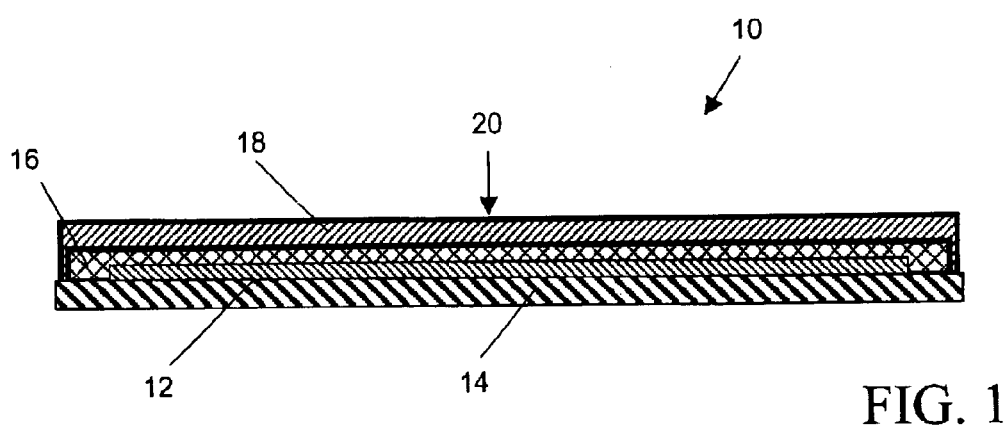
FIG. 1 is a cross-sectional view of one embodiment of a barrier coating deposited on a sensor device incorporating a protective overlayer between a sensing layer and the barrier coating.

In one embodiment, an analyte-permeability measurement method is disclosed that provides the capability to map spatial variations of permeability across a single barrier coating or an array of coatings. In this embodiment, a sensor layer that sorbs certain amount of analyte upon exposure to the analyte is incorporated in a solvent resistant sensor structure. An array of barrier coatings is applied onto the sensor or an array of barrier coatings is applied onto individual sensors. Upon exposure of the coating array to the analyte, the coating permeability is determined by the time-dependent change in the spectroscopic, viscoelastic, dielectric, or gravimetric signature of the sorbing sensor layer under the barrier coating. This detectable spectroscopic, viscoelastic, dielectric, or gravimetric signal is then compared to the signal produced from a reference spatial region containing a bare sensor layer or a reference coating material.

To achieve the stated and other advantages of the present invention, as embodied and described below, the invention includes a device for mapping of barrier coatings for their analyte-transport properties, the device comprising: a transducer having at least one external surface; a sensor layer applied to at least one of the at least one external surface of the transducer, a solvent-resistant overlayer applied onto the sensor layer; an array of barrier coatings deposited onto the individual overlayers or on a single overlayer incorporating the whole library; an analyte for exposure to the array of barrier coatings; a measurement device for measuring variation in signal of the sensor layer for the array of barrier coatings exposed to analyte; and a processor for analysis of the signals from the transducers.

In another embodiment, a water-vapor-permeability measurement method is disclosed that provides the capability to map spatial variations of permeability across a single barrier coating or an array of coatings. In this embodiment, a colorimetric and/or fluorescent reagent that exhibits a change in the absorption or/and luminescence spectrum, or another optical property, upon exposure to water vapor is incorporated in a solvent resistant sensor structure. An array of barrier coatings is applied onto the sensor or an array of barrier coatings is applied onto individual sensors. Upon exposure of the coating array to water vapor, the coating permeability is determined by the time-dependent change in the optical signature of the immobilized reagent under the barrier coating. This optical signal is then compared to the signal produced from a reference spatial region containing a bare sensor, i.e. having no barrier coating, or a reference coating material having known characteristics.

In yet another embodiment, an analyte-permeability measurement method is disclosed that provides the capability to map spatial variations of permeability across a single barrier coating or an array of coatings. In this embodiment, a layer that exhibits a change in the absorption or/and luminescence spectrum upon exposure to analyte fluid is incorporated in a solvent resistant sensor structure. An array of barrier coatings is applied onto the sensor or an array of barrier coatings is applied onto individual sensors. Upon exposure of the coating array to analyte fluid, the coating permeability is determined by the time-dependent change in the optical signature of the immobilized reagent under the barrier coating. This optical signal is then compared to the signal produced from a reference spatial region containing a bare sensor or a reference coating material.

Referring to FIG. 1, a sensor device 10 having a sensing layer 12 deposited on a substrate 14, and a protective overlayer 16 deposited on the sensing layer, may be used in the screening of a barrier property of one or more barrier coatings 18 with respect to one or more fluids 20.

The sensing layer 12 may be any material that does not change the properties of the deposited barrier coating 18 and/or the deposited overlayer 16, and that interacts with the fluid 20 in a manner that may be measured. As such, the combination of sensing layer 12 deposited on substrate 14 forms a sensor, such as an optical sensor, an acoustic wave sensor, a chemical resistor, a conductivity sensor, a microelectro-mechanical system (MEMS) sensor, an electrochemical sensor, etc. For example, an optical sensor may include a colorimetric sensor, a luminescent sensor, a chemi-luminescent sensor, a vacuum UV absorbance sensor, a UV-visible light ("UV-vis") absorbance sensor, an infrared absorbance sensor, a Raman sensor, an interferometric sensor, a polarization sensor, and a luminescence lifetime sensor. The interaction of sensing layer 12 with fluid 20 may change the associated sensor property, such as the optical signature. In another example, the interaction with the plurality of fluids may alter the characteristics of received radiation, or may produce luminescent radiation, or combinations of both. The composition of the sensing layer varies depending on the particular barrier property and barrier coating being analyzed, as well as the particular fluid and transducer type being used. Characteristics of the sensing layer, such as absorption spectrum, refractive index, luminescence intensity, luminescence lifetime, luminescence spectrum, acoustic wave properties, dielectric properties, viscoelastic properties, morphological properties, etc., may change upon exposure to any one of the fluids. Further, to enhance the ability to detect the changes or impacts on radiation, a chemically sensitive dye may be incorporated into the sensing film and optionally into the barrier coating, or a dye molecule may be directly attached to a matrix molecule. In this manner, changes of optical properties of the dye are relatable to the variation of the chemical environment of the barrier coating. Therefore, as the change in barrier properties are associated with a penetration of the barrier coating by at least one of the plurality of fluids, the measured change or impact on the sensing layer corresponds to a barrier property metric for the given coating with respect to the at least one fluid.

The sensing layer 12 may include, for example, a fluid-sensitive material, a calorimetric or fluorescent dye, a calorimetric or fluorescent dye where its optical property is modulated by presence of an analyte fluid, and combinations thereof. The sensing layer 12 is a thin film, suitably of a thickness from about 0.001 1000 micrometers, particularly from about 0.005 500 micrometers, and more particularly from about 0.01 100 micrometers.

The substrate 14 may be any material that does not interact with the sensing layer 12. Substrate may include a transducer surface. Additionally, substrate 14 may include a fluid-permeable substrate or a fluid-impermeable substrate. Suitable examples of substrate 14 include, but are not limited to metals, semiconductors, polymers, glass, piezoelectric materials such as quartz, lithium niobate, nitride, lithium tantalate, bismuth germanium oxide, aluminum nitride, or gallium arsenide, and acoustic-wave films (ZnO and AlN), etc.

The protective overlayer 16 may comprise a chemically-resistant, and preferably a solvent-resistant material, that allows transport of the fluid 20 to the sensing layer 12 but that is not destroyed or substantially altered by any of the barrier coatings 18. Suitable examples of a protective overlayer 16 include, for example, amorphous fluoropolymers.

As another example, can be a sol-gel film. Another material can be any heavily cross linked polymer overlayer film, for example polyimide.

The barrier coating 18 may include any material for which a barrier property with respect to a given fluid is desired to be quantified. A suitable barrier coating may include, but is not limited to, any organic material, more preferably polymers with additives, polycarbonates, polycarbonate blends, silicones, polycarbonate-polyorganosiloxane copolymers, polyetherimide resins, oxides, nitrides and oxinitrides of silicon, aluminum, zinc, boron and other metals, ceramics, polyvinyl alcohol, ethylene vinyl alcohol copolymers, polyvinyl dichloride, sol-gels, different types of nylon, cellophane, polyethylene terephtalate, PVC, PCTFE, polypropylene, any new materials developed using combinatorial chemistry approaches, and combinations thereof, as well as other similar materials typically used to provide a barrier to transport of a given fluid. The barrier coating suitably has a thickness from 0.1 nm to 100 micrometers, particularly from 1 nm to 10 micrometers, and more particularly from 10 nm to 1 micrometer. Further, the sample size of each barrier coating may vary, depending on the size of the transducer and depending on the capabilities of the detecting equipment. A suitable sample size for each of a plurality of barrier coatings is in the range of about 1 square micrometer 1 square meter, more particularly about 100 square micrometers 100 square centimeters, and most particularly about 1 square millimeter 10 square centimeters.

The fluid 20 may include a material in any phase that is generally harmful to, or that may be harmed by, a material covered by the coating. Suitable fluids usable in conjunction with the present invention include, but are not limited to, oxygen; water vapor; ammonia; carbon dioxide; carbon monoxide; ethylene oxide; helium; hydrogen; hydrogen sulfide; methyl bromide; nitrogen; sulfur dioxide; fuels; alkaline and acidic solutions; water; organic solvents of different polarity; solvent mixtures; gasoline; mixtures containing hexane; a hexane/toluene mixture; ketones such as methdyl amyl ketone; glycol ethers such as 2-butoxyethoanol; glycol ether esters such as ethyl-3-ethoxy-propionate (EEP) and methoxy propyl acetate; toluene; methylethyl ketone (MEK); ester solvents such as ethyl acetate, butyl acetate, propyl acetate, and the like; alcohols such as butanol; 1-methyl-2-pyrrolidinone; xylenes; and other volatile inert solvents.

Figure 2:
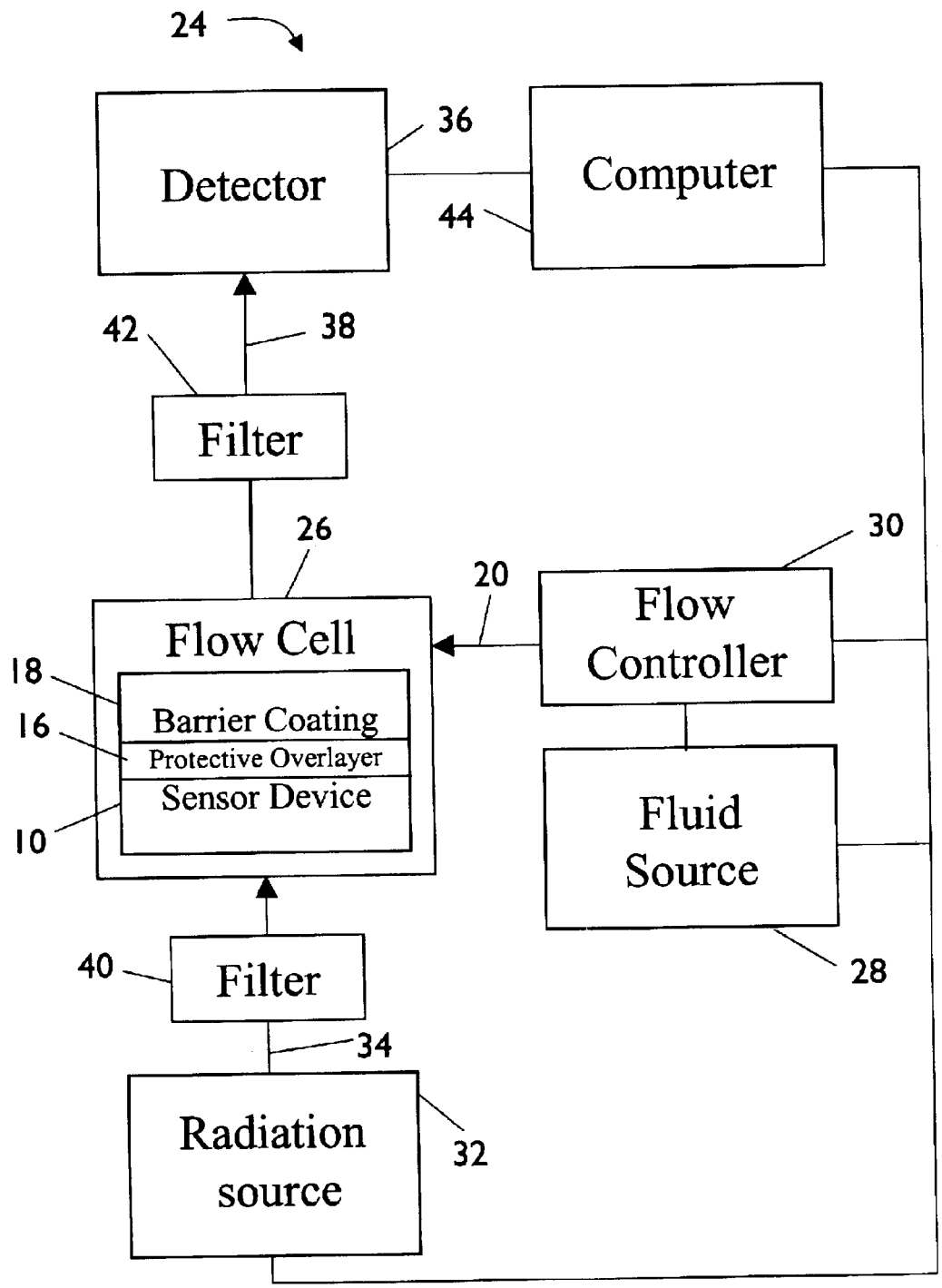
FIG. 2 is a functional diagram of one embodiment of a screening system for evaluating a barrier property of a barrier coating deposited on the sensor device of FIG. 1.

Referring to FIG. 2, one embodiment of a screening system 24 for evaluating a barrier property of a coating includes one or more barrier coatings 18 deposited on one or more sensor devices 10. Each coating 18 and sensor device 10 are disposed within a flow cell 26, which sealingly contains one or more fluids 20 that are controllingly-delivered from one or more fluid sources 28 via one or more flow controllers 30. A radiation source 32 directs a reference radiation 34 having predefined properties toward the coatings 18, and a detector 36 measures the properties of the resulting radiation 38. Wavelength selection devices such as filters, monochromators, and others 40 and 42 may be respectively positioned between the radiation source and the coating, and between the coating and the detector, to filter the radiation into a predetermined range of characteristics. A processing device 44, such as a computer having suitable software, may control the system and analyzes the measurement of the resulting radiation 38 to determine the barrier property of each coating 18 and the relative performance of each coating with respect to the fluid 20.

The change in optical properties of radiation interacting with the barrier coating may be attributed to penetration of the barrier coating by at least one of the plurality of fluids. The change in optical properties of the radiation caused by a fluid partitioned or interacted into the sensing layer, is detectable as a change in such properties as absorbance, scattering, refractive index, optical thickness, or luminescence. The impact on the radiation is defined as a measurable change in the radiation, such as a variation in amplitude, frequency, polarization state, phase and temporal properties of the wave. The reference radiation 34 has a predetermined range of one or more characteristics, including intensity, wavelength, polarization state, phase and temporal properties. For example, the predetermined range for intensity may be in the range of about a single photon to about 1000 kilowatts, or from about a single photon to about 1 kilowatt. For wavelength, from about 10 nanometers–50 micrometers, or from about 150 nanometers 20 micrometers. For polarization state, from about 0 to 360 degrees. For phase difference, from about 0.001 to 10000 wavelengths of probe radiation, preferably from about 0.01 to 1000 wavelengths of probe radiation, and most preferably from about 0.1 to 100 wavelengths of probe radiation. For a temporal property such as luminescence lifetime, from about 10 picoseconds–1000 seconds, preferably about 100 picoseconds–1 second, and more preferably about 1 nanosecond 100 milliseconds. For a temporal property such as time delay, from about 1 femtosecond–1000 seconds, preferably about 100 femtoseconds–1 second, and more preferably from about 10 picoseconds 100 milliseconds.

For example, the reference radiation 34 may be a pulsed wave or a continuous wave of radiation. Similarly, the resulting radiation 38 has a predetermined range of one or more characteristics, including amplitude, frequency, wavelength, polarization state, phase and temporal properties, as mentioned above. For both the reference radiation 34 and the resulting radiation 38, the predetermined range of characteristics may vary depending on the barrier coating 18, sensing layer 12, fluids 20 and detection/measuring capabilities being utilized. Further, for the resulting radiation 38, the measured value of one or more of the characteristics may be utilized to determine the relative barrier property of the coating with respect to a given fluid.

For example, in detecting luminescence, the reference radiation 34 has a predetermined range of characteristics that excite the sensing layer 12 if exposed to any given one of the fluids 20, thereby promoting luminescence and providing the resulting radiation 38. The resulting radiation 38 is typically of a substantially different intensity relative to excitation radiation, when exposed to one or more fluids 20, than the reference radiation 34 and the value of, for example, its intensity may be correlated to a barrier property of the coating with respect to any given one of the fluids 20.

Similarly, the resulting radiation 38 is typically of a substantially different wavelength relative to excitation radiation, when exposed to one or more fluids 20, than the reference radiation 34 and the value of, for example, its wavelength may be correlated to a barrier property of the coating with respect to any given one of the fluids 20.

Similarly, the resulting radiation 38 is typically of a substantially different polarization relative to excitation radiation, when exposed to one or more fluids 20, than the reference radiation 34 and the value of, for example, its polarization may be correlated to a barrier property of the coating with respect to any given one of the fluids 20.

Similarly, the resulting radiation 38 is typically of a substantially different phase relative to excitation radiation, when exposed to one or more fluids 20, than the reference radiation 34 and the value of, for example, its phase may be correlated to a barrier property of the coating with respect to any given one of the fluids 20.

Similarly, the resulting radiation 38 is typically of a substantially different temporal property such as luminescence lifetime relative to excitation radiation, when exposed to one or more fluids 20, than the reference radiation 34 and the value of, for example, its temporal property such as luminescence lifetime may be correlated to a barrier property of the coating with respect to any given one of the fluids 20.

The radiation source 32 is any device capable of generating a radiation having a predetermined set of characteristics. Suitable examples of radiation source 34 include, but are not limited to, those listed in Table 1.

TABLE 1

Useful Radiation sources.

| Source | Spectral range of emission |
|---|---|
| Continuous wave sources: | |
| Xenon arc lamp | 200–1000 nm |
| Mercury arc lamp | 250–600 nm |
| Deuterium lamp | 180–420 nm |
| Tungsten lamp | 320–2500 nm |
| Light emitting diodes | different diodes cover range from 370 to 1500 nm different diode lasers cover range from about 400 to 1500 nm |
| Diode lasers | nm |
| Argon ion laser | several lines over 350–514 nm |
| Helium-neon laser | several lines over 543–633 nm |
| Krypton laser | several lines over 530–676 nm |
| Pulsed sources: | |
| Excimer lasers | 157, 193, 248, 308, 351 nm |
| Nitrogen laser | 337 nm |
| Nd: YAG laser | fundamental - 1064 nm, frequency doubled - 532 nm, tripled - 355 nm, quadrupled - 266 nm |
| Ti: Sapphire laser | 720–1000, frequency doubled 360–500 nm |
| Dye lasers | 360–990 frequency doubled 235 to 345 nm |

The detector 36 is any device capable of receiving and measuring the value of at least one characteristic of the resulting radiation 38. Suitable examples of detector 36 include, but are not limited to, a CCD camera, photomultiplier tube, avalanche photodiode, etc.

The flow cell 26 is any device having a sealable chamber for containing any of the plurality of fluids and the barrier coatings. The flow cell 26 may be sized to further contain the radiation source 32, detector 36 and other components of the system as well. If the radiation source 32 and detector 36 are maintained on the exterior of the flow cell 26, then the flow cell may be constructed of a radiation-transmissible material, at least in areas adjacent to the radiation source and the detector.

The filters 40 and 42 may include any device that defines a given characteristic of the radiation. Suitable examples of filters 40 and 42 include, but are not limited to, a monochromator (such as SLM Instruments, Inc., Urbana, Ill., Model FP-092), and/or one or more optic interference, long-pass, short-pass, or wide band-pass filters. The filter may include a liquid filter to block near-infrared radiation (such as Oriel Instruments, Stratford, Conn., Model 61945), colored-glass, a contrast-enhancement filter, a broadband filter, a dichroic filter, a laser-line filter, a long-wavepass filter, a narrowband filter, a short-wavepass filter, a neutral density filter, a tunable filter, and others. Representative manufacturers include Melles Griot, Inc., Irvine, Calif.; Kaiser Optical Systems, Inc., Ann Arbor, Mich.; Coherent Auburn Group, Auburn, Calif.; CVI Laser Corp., Albuquerque, N.Mex.; Newport Corp., Irvine, Calif.; and Omega Optical, Inc., Battleboro, Vt.

The processing device 44 may be a computer or any other processing device having capabilities such as inputs, outputs, software, firmware and hardware for performing the analysis discussed herein and optionally for managing the operation of the entire system. The processing device 40 may be a personal computer, a workstation, a personal digital assistant, a super computer, or a processor built into or otherwise associated with one of the components of the system such as the detector.

Figure 3:
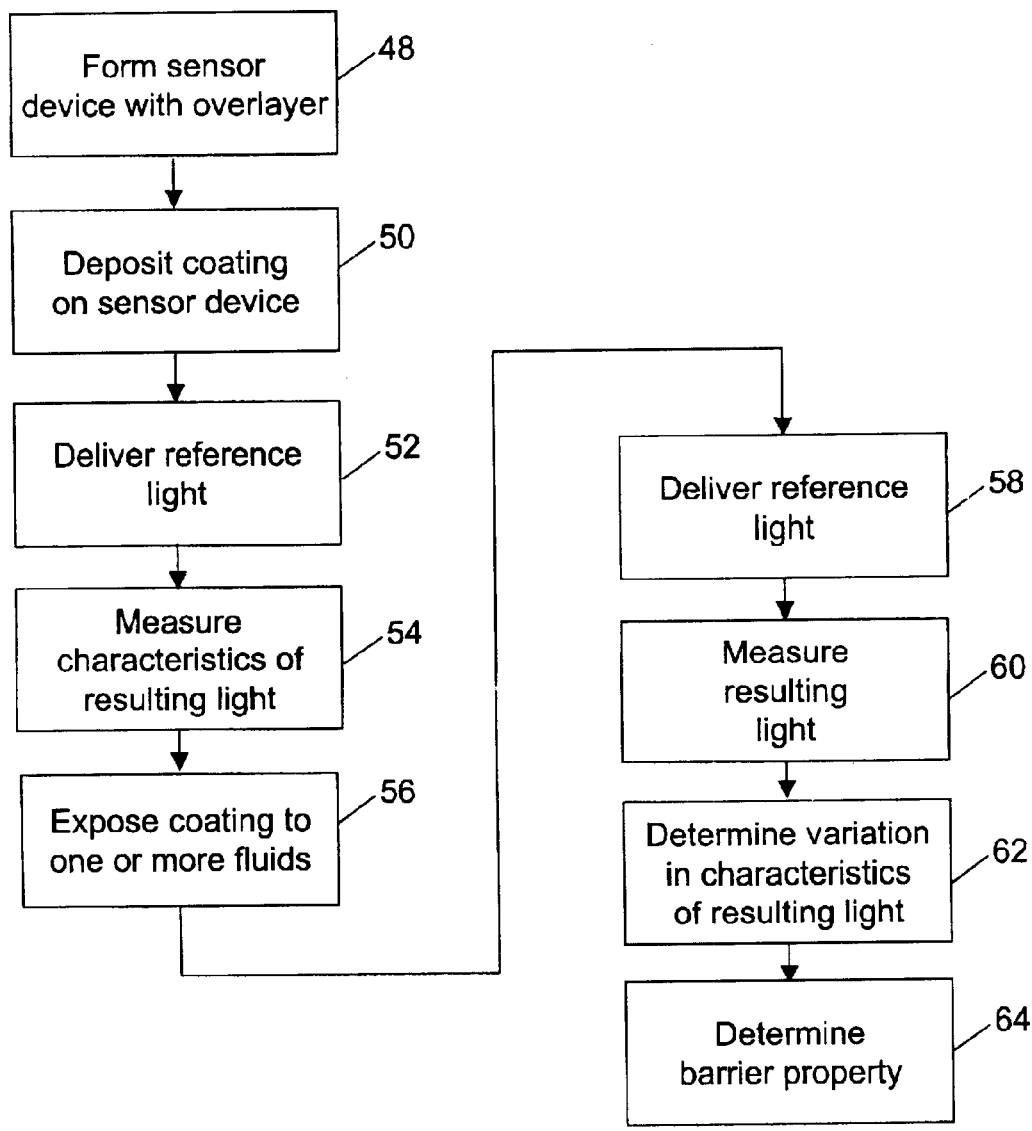
FIG. 3 is a block diagram representing one embodiment of a method of determining a barrier property of a barrier coating.

Referring to FIG. 3, one embodiment of a method to determine a barrier property of a coating includes forming the sensor device having the protective overlayer (Block 48). Then, the barrier coating is deposited on the sensor device (Block 50). The sensor with coating may be optionally cured, if required. Then, the reference radiation is delivered to the coating (Block 52) and the initial characteristics of the resulting radiation are detected and measured (Block 54). Then, the coating is exposed to one or more of the plurality of fluids for a predetermined amount of time (Block 56). The predetermined amount of time may be a set, given time period or it may be a time period that corresponds to a predetermined amount of penetration of the barrier coating by one or more of the fluids. The reference radiation is again delivered to the coating (Block 58) and the subsequent characteristics of the resulting radiation are detected and measured (Block 60). Further, any variation between the initial and subsequent characteristics of the resulting radiation is determined (Block 62) and, based on the variation, a relative barrier property metric for the barrier coating with respect to the fluid is determined (Block 64).

In an embodiment of the present invention, for measurements of oxygen transport, a fluorophore that exhibits fluorescent quenching upon exposure to molecular oxygen is incorporated in a solvent resistant sensor structure. The luminescence intensity and lifetime of such fluorophores typically decrease as the concentration and/or partial pressure of oxygen increases. This luminescence response thereby serves as a robust and predictable metric for the amount of oxygen around the fluorophore. Such a fluorophore is incorporable into a sensor, and such a solid-state oxygen sensor is used in one embodiment, for example, for quantitation of oxygen transport. See, e.g., Potyrailo, R. A.; Hieftje, G. M., Oxygen detection by fluorescence quenching of tetraphenylporphyrin immobilized in the original cladding of an optical fiber, Anal. Chim. Acta 1998, 370, 1–8; Potyrailo, R. A.; Hieftje, G. M., Use of the original silicone cladding of an optical fiber as a reagent-immobilization medium for intrinsic chemical sensors, Fresenius' J. Anal. Chem. 1999, 364, 32–40; Amao, Y.; Asai, K.; Miyashita, T.; Okura, I., Novel optical oxygen pressure sensing materials:

platinum porphyrin-styrene-trifluoroethylmethacrylate copolymer film, Chem. Lett. 1999, 1031–1032; Amao, Y.; Asai, K.; Okura, I.; Shinohara, H.; Nishide, H., Platinum porphyrin embedded in poly(1-trimethylsilyl-1-propyne) film as an optical sensor for trace analysis of oxygen, Analyst 2000, 125, 1911–1914ln an embodiment of the present invention, to measure, for example, oxygen permeability, an array of barrier coatings is applied onto the sensor. Upon exposure of the coating array to oxygen, the coating permeability is determined by the time-dependent change in the luminescence signature of the immobilized fluorophore under the barrier coating. This luminescence signal is then compared, for example, to the signal produced from a reference spatial region containing a bare sensor or a reference coating material.

Figure 4:
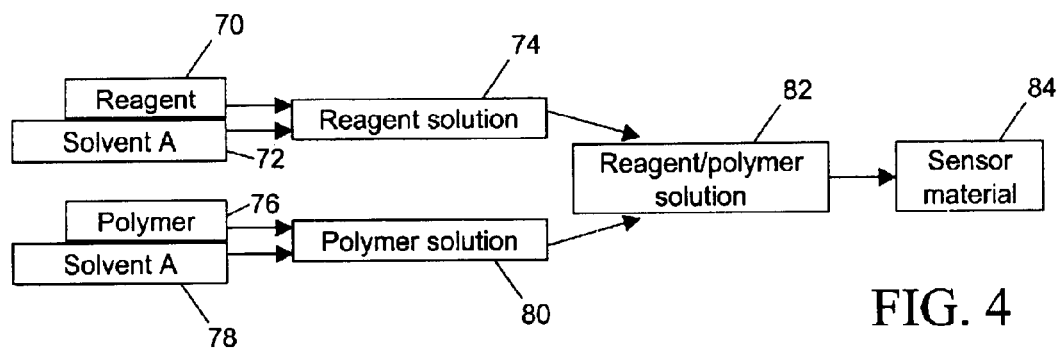
FIGS. 4 and 5 are functional block diagrams representing embodiments of methodologies of fabricating sensor devices.
Figure 5:
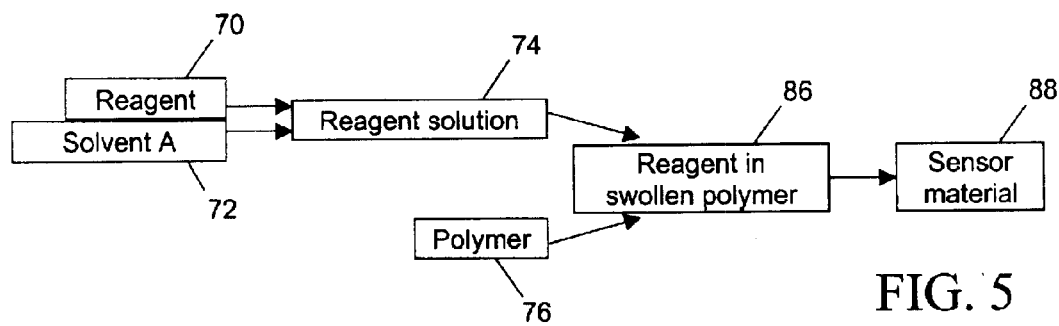

To incorporate a fluorophore into a solid polymer material, two methods are usable in conjunction with the present invention, as illustrated in FIGS. 4 and 5. In an embodiment of the present invention, a reagent is immobilized into the polymer matrix from a reagent solution in an organic solvent. FIGS. 4 and 5 present fabrication events for a chemical sensor with a reagent immobilized into a polymer film. As shown in FIG. 4, a reagent 70, including the fluorophore, is mixed with a solvent 72 to produce a reagent solution 74. A polymer 76 is mixed with a solvent 78 to produce a polymer solution 80. Solvents can be either polar or non polar, including but not limited to, water, ethanol, methanol, acetone, chloroform, toluene, benzene, and hexane. The reagent solution 74 and the polymer solution 80 are mixed to produce a reagent/polymer solution 82, and a sensor material 84 is produced from a polymer solution after film casting. In FIG. 5, the reagent 70 is mixed with solvent 72 to produce reagent solution 74. Polymer 76 is mixed with the reagent solution 74 to produce a reagent in swollen polymer 86. A sensor material 88 is produced from a polymer swollen in a reagent solution after film drying.

For reagent immobilization, a variety of materials is used. These include polymers, such as silicones, styrene-trifluoroethylmethacrylate copolymer, poly(1-trimethylsilyl-1-propyne), polystyrene, polymethylmethacrylate, and many others including their blends and copolymers. For details, see, Wolfbeis, O. S. In Fiber Optic Chemical Sensors and Biosensors; O. S. Wolfbeis, Ed.; CRC Press: Boca Raton, Fla., 1991; Vol. 2; pp 19–53; Potyrailo, R. A.; Hieftje, G. M., Oxygen detection by fluorescence quenching of tetraphenylporphyrin immobilized in the original cladding of an optical fiber, Anal. Chim. Acta 1998, 370, 1–8; Potyrailo, R. A.; Hieftje, G. M., Use of the original silicone cladding of an optical fiber as a reagent-immobilization medium for intrinsic chemical sensors, Fresenius' J. Anal. Chem. 1999, 364, 32–40; Amao, Y.; Asai, K.; Miyashita, T.; Okura, I., Novel optical oxygen pressure sensing materials: platinum porphyrin-styrene-trifluoroethylmethacrylate copolymer film, Chem. Lett. 1999, 1031–1032; Amao, Y.; Asai, K.; Okura, I.; Shinohara, H.; Nishide, H., Platinum porphyrin embedded in poly(1-trimethylsilyl-1-propyne) film as an optical sensor for trace analysis of oxygen, Analyst 2000, 125, 1911–1914.

With these processes, however, if a library of barrier coatings is applied onto a sensor, the sensor film can be destroyed if the barrier coating solution has properties similar to the reagent solution. To eliminate this problem, the present invention employs the thin overlayer on top of an oxygen-sensitive film, as shown in FIG. 1. The thin overlayer is deposited on top of the sensing layer to protect the sensing layer from the solvent of the barrier coating formulation.

In an embodiment of the present invention, the protective overlayer 16 includes, for example, a random copolymer of tetrafluoroethylene (TEF) and perfluoro-2,2-dimethyl-1,3-dioxole (PDD) sold under the trademark Teflon® AF. For film deposition of the protective overlayer 16, in an embodiment of the present invention, amorphous fluoropolymer is dissolved in perfluoro (2-butyl tetrahydrofuran), and a thin film from polymer solution is deposited onto the surface of the sensing layer 12. The present invention demonstrates several attractive features of amorphous fluoropolymers for the use as protective overlayers for chemical sensors. Unlike polymers used for reagent immobilization, films made of amorphous fluoropolymers are extremely stable upon exposure even to nonpolar solvents that completely dissolve conventional polymeric films with immobilized reagents.

As a result, with this embodiment, highly robust chemical sensors and sensor arrays are producible using these materials. For example, the presence of the protective overlayer on in between the sensing layer and the barrier coating does not noticeably increase the response time of a sensor without the protective overlayer. In one embodiment, for example, the permeability of oxygen in Teflon® AF materials is 80 235 times higher than in conventional polytetrafluoroethylene (PTFE) and thus does not noticeably increase the response time of an oxygen sensor.

Figure 6:
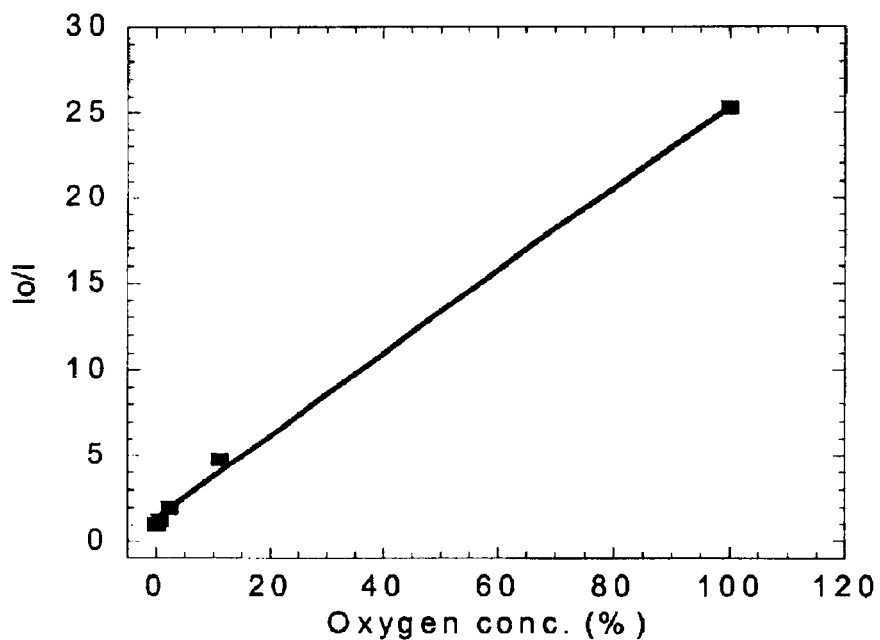
FIG. 6 is a Stern-Volmer quenching plot for one embodiment of a sensor of the present invention.
Figure 7:
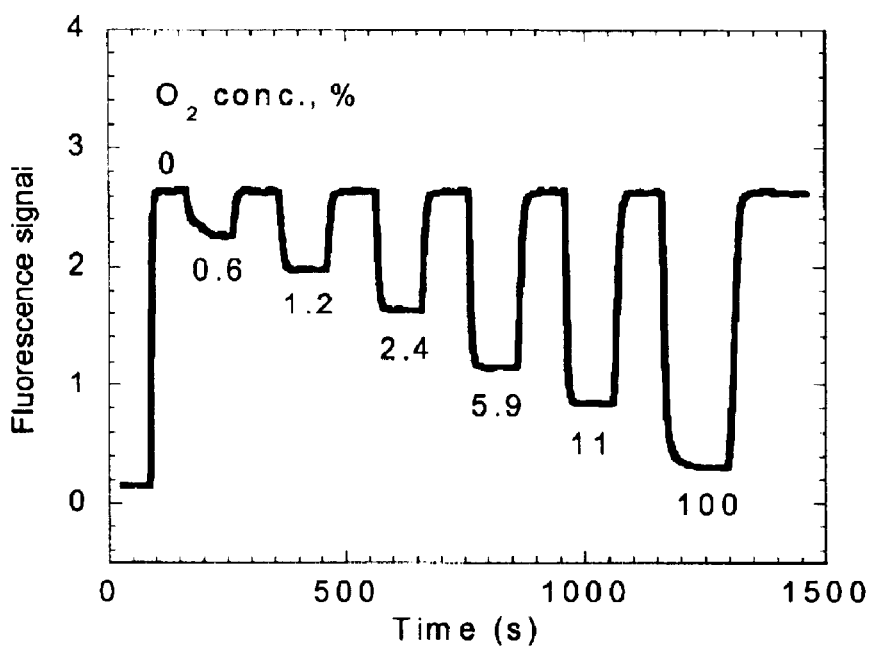
FIG. 7 is a plot of luminescence signal versus time showing reversible performance for one embodiment of a sensor of the present invention.
Figure 8:
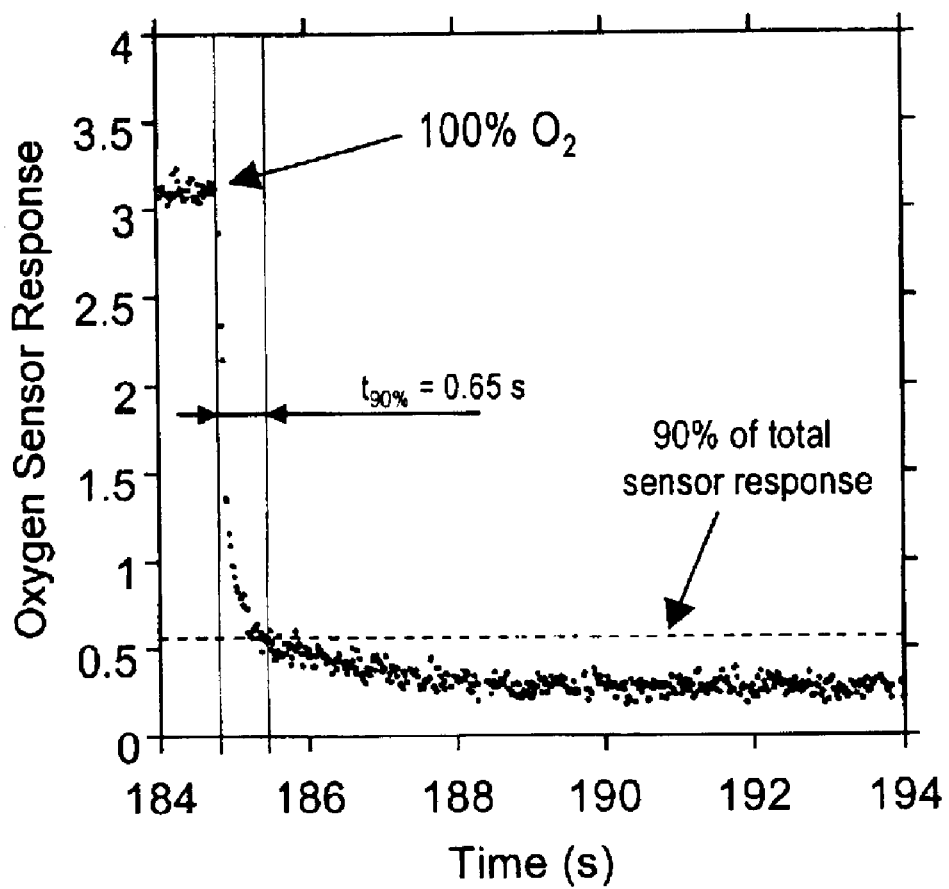
FIG. 8 is a plot of sensor response versus time for one embodiment of a sensor of the present invention.

In this embodiment of an oxygen sensor, the sensor material may be made of a polymer poly(methyl methacrylate)(PMMA) polymer with an immobilized platinum (II) octaethylporphyrin fluorophore. This fluorophore is known to provide an efficient quenching by molecular oxygen in a variety of polymer matrices. Sensor response was very sensitive with the Stern-Volmer quenching constant of 0.03 Torr $^{-1}$, as demonstrated by the results shown in FIG. 6, a Stern-Volmer quenching plot for the oxygen sensor based on a platinum (II) octaethylporphyrin fluorophore immobilized in a PMMA film and coated with a Teflon® AF overlayer. The sensor demonstrated a completely reversible performance as shown in FIG. 7. The response time of the sensor was very fast, $t_{90\%}=0.65s$, as shown in FIG. 8.

Different classes of chemically sensitive reagents are useful. One class of reagents includes porphyrins. Examples of suitable porphyrins include but are not limited to tetraphenylporphyrin, metal porphyrins, such as platinum (II) octaethylporphyrin (Pt-OEP) and palladium(II) octaethylporphyrin (Pd-OEP), and others as described in P. Hartmann, W. Trettnak, "Effects of polymer matrices on calibration functions of luminescent oxygen sensors based on porphyrin ketone complexes," Anal. Chem. 1996, 68, 2615–2620; A. Mills, A. Lepre, "Controlling the response characteristics of luminescent porphyrin plastic film sensors for oxygen," Anal. Chem. 1997, 69, 4653–4659; Potyrailo, R. A.; Hieftje, G. M., Oxygen detection by fluorescence quenching of tetraphenylporphyrin immobilized in the original cladding of an optical fiber, Anal. Chim. Acta 1998, 370, 1–8.

Another class of reagents includes polycyclic aromatic hydrocarbons. Examples and applications of this class of fluorophores are described by: I. B. Berlman, Handbook of luminescence spectra of aromatic molecules, Academic Press, New York, N.Y., 1971; O. S. Wolfbeis, Fiber Optic Chemical Sensors and Biosensors; O. S. Wolfbeis, Ed.; CRC Press: Boca Raton, Fla., 1991; Vol. 2; pp 19–53; Hobbs, S. E.; Potyrailo, R. A.; Hieftje, G. M., Scintillator light source for chemical sensing in the near-ultraviolet, Anal. Chem. 1997, 69, 3375–3379. Preferred fluorophores of this class include pyrene, pyrenebutyric acid, fluoranthene, decacyclene, diphenylanthracene, and benzo(g,h,l)perylene.

Another class of reagents includes a variety of long-wave absorbing dyes such as perylene dibutyrate, and heterocycles including fluorescent yellow, trypaflavin and other heterocycle compounds as described by: O. S. Wolfbeis, Fiber Optic Chemical Sensors and Biosensors; O. S. Wolfbeis, Ed.; CRC Press: Boca Raton, Fla., 1991; Vol. 2; pp 19–53.

Yet another group of reagents includes metal-organic complexes of ruthenium, osmium, iridium, gold and platinum as described by: O. S. Wolfbeis, Fiber Optic Chemical Sensors and Biosensors; O. S. Wolfbeis, Ed.; CRC Press: Boca Raton, Fla., 1991; Vol. 2; pp 19–53, J. N. Demas, B. A. Degraff, P. B. Coleman, "Oxygen sensors based on luminescence quenching," Anal. Chem. 1999, 71, 793A–800A; J. N. Demas, B. A. DeGraff, "Design and applications of highly luminescent transition metal complexes," Anal. Chem. 1991, 63, 829A–837A; A. Mills, A. Lepre, B. R. Theobald, E. Slade, B. A. Murrer, "Use of luminescent gold compounds in the design of thin-film oxygen sensors," Anal. Chem. 1997, 69, 2842–2847; Potyrailo, R. A.; Hieftje, G. M., Use of the original silicone cladding of an optical fiber as a reagent-immobilization medium for intrinsic chemical sensors, Fresenius' J. Anal. Chem. 1999, 364, 32–40. Yet another group of reagents includes solvatochromic dyes as extensively reviewed in, for example, C. Reichardt, Chemical Reviews, volume 94, pages 2319–2358 (1994). Preferred fluorescent solvatochromic dyes have a luminescence quantum yield of greater than about 0.01. Other characteristics of the dyes include positive and negative solvatochromism which corresponds to the bathochromic and hypsochromic shifts, respectively of the emission band with increasing solvent polarity. In addition to the solvent-induced spectral shifts of the emission spectra, some dyes exhibit the solvent-dependent ratio of emission intensities of two luminescence bands. One such solvatochromic dye is pyrene. Some examples of preferred solvatochromic dyes include 4-dicyanmethylene-2-methyl-6-(p-dimethylaminostyryl)-4H-pyran (DCM; CAS Registry No. 51325-91-8); 6-propionyl-2-(dimethylamino)naphthalene (PRODAN; CAS Registry No. 70504-01-7); 9-(diethylamino)-5H-benzo[a]phenoxazin-5-one (Nile Red; CAS Registry No. 7385-67-3); phenol blue; stilbazolium dyes; coumarin dyes; ketocyanine dyes, including CAS Registry No. 63285-01-8; Reichardt's dyes including Reichardt's Betaine dye (2,6-diphenyl-4-(2,4,6-triphenylpyridinio) phenolate; CAS Registry No. 10081-39-7); merocyanine dyes, including merocyanine 540 (CAS Registry No. 62796-23-0); so-called $\pi^*$ dyes, including N,N-dimethyl-4-nitroaniline (NDMNA; CAS Registry No. 100-23-2) and N-methyl-2-nitroaniline (NM2NA; CAS Registry No. 612-28-2); and the like. Applications of solvatochromic dyes for monitoring of moisture are described for example in Sadaoka, Y.; Matsuguchi, M.; Sakai, Y.; Murata, Y. -U., Optical humidity sensor using Reichardt's betain dye-polymer composites, Chem. Lett. 1992, 53–56; Sadaoka, Y.; Sakai, Y.; Murata, Y., Optical humidity and ammonia gas sensors using Reichardt's dye-polymer composites, Talanta 1992, 39, 1675–1679; Potyrailo, R. A.; Hieftje, G. M., Use of the original silicone cladding of an optical fiber as a reagent-immobilization medium for intrinsic chemical sensors, Fresenius' J. Anal. Chem. 1999, 364, 32–40.

Yet another group of reagents includes calorimetric and luminescent acid-base and cationic reagents as extensively reviewed in, for example, Kolthoff, I. M. Acid-Base Indicators; The MacMillan Company: New York, 1937; Bacci, M.; Baldini, F.; Bracci, S., Spectroscopic behavior of acid-base indicators after immobilization on glass supports, Appl. Spectrosc. 1991, 45, 1508–1515; Sadaoka, Y.; Matsuguchi, M.; Sakai, Y.; Murata, Y. -U., Optical humidity sensing characteristics of Nafion-dyes composite thin films, Sens. Actuators B 1992, 7, 443–446; Sadaoka, Y.; Sakai, Y.; Murata, Y., Optical properties of cresyl violet-polymer composites for quantification of humidity and ammonia gas in ambient air, J. Mater. Chem. 1993, 3, 247–251; Zinger, B.; Shier, P., Spectroscopic studies of cationic dyes in Nafion, Preliminary investigation of a new sensor for hydrophilic contamination in organic solvents, Sens. Actuators B 1999, 56, 206–214; Haugland, R. P. Handbook of Fluorescent Probes and Research Chemicals; Molecular Probes: Eugene, Oreg., 1996. Some of these dyes are thymol blue, congo red, methyl orange, bromocresol green, methyl red, bromocresol purple, bromothymol blue, cresol red, phenolphthalein, SNAFL indicators, SNARF indicators, 8-hydroxypyrene-1, 3,6-trisulfonic acid, fluorescein and its derivatives, oregon green, and a variety of dyes mostly used as laser dyes including rhodamine dyes, styryl dyes, cyanine dyes, and a large variety of other dyes. These reagents may also be referred to as pH reagents.

Yet another group of reagents includes oxygen-sensitive calorimetric reagents. Some reagents useful for calorimetric determinations of molecular oxygen are reviewed in Chemical Detection of Gaseous Pollutants; Ruch, W. E., Ed.; Ann Arbor Science Publishers: Ann Arbor, Mich., 1968. These include, among others, 2,4-diaminophenol dihydrochloride, manganous oxide, combination of manganous hydroxide and potassium iodide containing starch, ferrous salt in combination with methylene blue, reduced form of sodium anthraquinone-B-sulfonate, reduced form of ammonium anthraquinone-2-sulfonate, carbohydrate of Tschitschibabin, alkaline pyrogallol, and ammoniacal cuprous chloride.

Yet another group of reagents includes oxygen-sensitive chemoluminescent reagents. Some reagents useful for chemoluminescent determinations of molecular oxygen are reviewed in: O. S. Wolfbeis, Fiber Optic Chemical Sensors and Biosensors; O. S. Wolfbeis, Ed.; CRC Press: Boca Raton, Fla., 1991; Vol. 2; pp 19–53. Among others, useful chemoluminescent compounds for oxygen determinations are poly(ethylene-2,6-naphthalene-dicarboxylate), tetraamino-ethylenes without aromatic functions, and many others. For spatial mapping of oxygen permeability through a library of barrier coatings, barrier coatings are deposited on top of the overlayer of the oxygen sensor. The sensor is then exposed to an analyte, such as varying concentrations or partial pressures of oxygen. For example, the sensor can be exposed first to the atmosphere at which the coating deposition was performed, and then to nitrogen or oxygen. The difference in a given sensor property may then be determined, such as the change in luminescence intensity or lifetime. A comparison of luminescence values is made for the coating library exposed to different concentrations of oxygen at different times.

Figure 9:
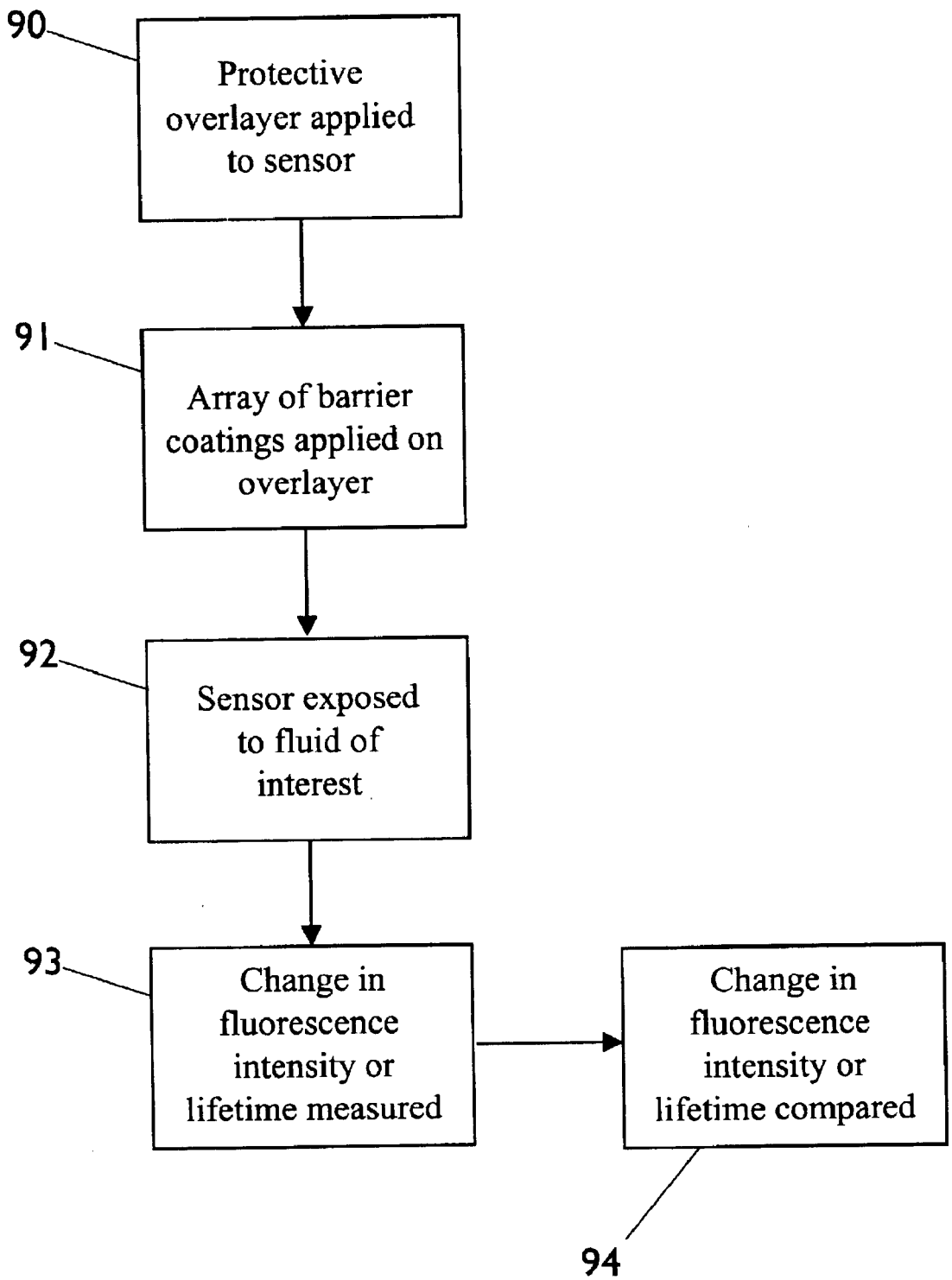
FIG. 9 is a functional block diagram of one embodiment of a method for mapping a barrier property of a barrier coating.

A function diagram of spatial mapping of oxygen permeability in accordance with an embodiment of the present invention is shown in FIG. 9. A protective overlayer is applied to an oxygen sensor (block 90). An array of barrier coatings is applied to the protective overlayer (block 91). The coated sensor is exposed to varying concentrations of a fluid of interest, such as oxygen (block 92). The change in optical signal, such as luminescence intensity or lifetime or other optical property, of an immobilized reagent in a sensing layer of the sensor is then measured across each barrier coating (block 93) and compared (block 94) to determine a relative performance of each barrier coating.

Figure 10:
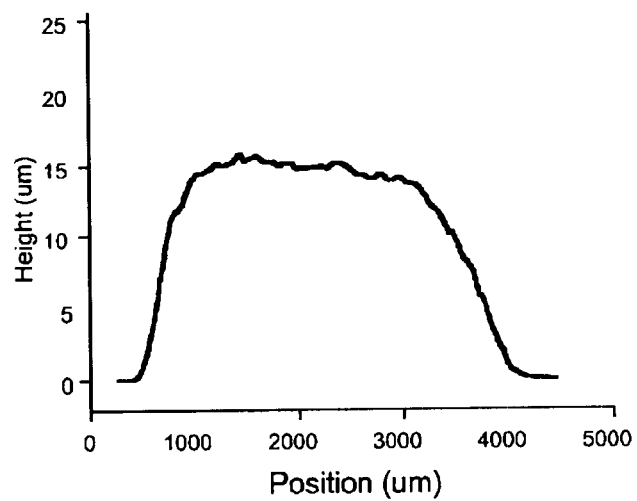
FIG. 10 is a graph of the coating thickness of one embodiment one element of an array of barrier coatings.

An evaluation of this technique was performed by depositing an array of polycarbonate (PC) coatings from a solution of polycarbonate in chloroform through a mask to yield circular coating regions. An array of polycarbonate coatings was deposited onto an oxygen-sensitive layer for luminescence mapping of oxygen permeability. In this example, each circular coating was approximately 3 mm in diameter. FIG. 10 shows the thickness profile of a single element in the array of coatings.

Figure 11:
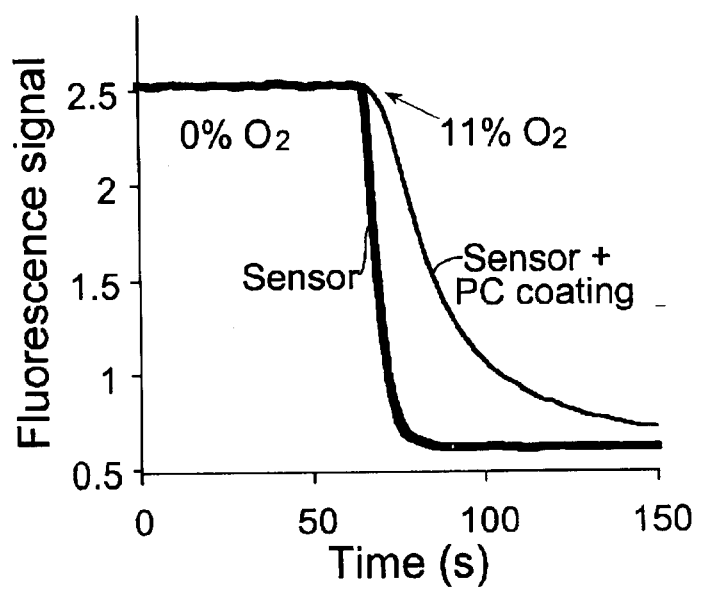
FIG. 11 is a graph comparing the dynamic response of reference and polycarbonate-coated regions of an oxygen sensor.

In an embodiment of the present invention, luminescence of the immobilized fluorophore was excited using a 450-W Xe arc lamp coupled to a monochromator set at 380 nm. Luminescence signal was measured at 650 nm. Comparison of the dynamic response of the reference and PC-coated regions of the oxygen sensor is presented in FIG. 11. This data illustrates that luminescence measurements of the array of coatings performed at different delays upon the change in oxygen concentration result in the capability to map permeability properties of the coating array when the coating is deposited onto a nonpermeable substrate.

In another example performed in accordance with embodiments of the present invention, luminescence mapping was performed using a setup which included a white light source (450-W Xe arc lamp, SLM Instruments, Inc., Urbana, Ill., Model FP-024), a monochromator for selection of the excitation wavelength (SLM Instruments, Inc., Model FP-092), and a CCD camera (Roper Scientific, Trenton, N.J., Model TE/CCD 1100 PF/UV). The excitation wavelength for the luminophore was selected using the monochromator and was directed to the sample. Sample luminescence was collected with the camera with an integration time of 1 s. The excitation light was filtered out from being captured by the camera using a long pass optical filter (610-nm cut-off).

A ratio of two images when the sensor is exposed to nitrogen ($I_o$) and oxygen (I) represent an oxygen-permeability map The high levels of signal demonstrate that the luminescence was efficiently quenched upon exposure to oxygen from its original high level in nitrogen atmosphere. A ratio of two images when the sensor was exposed to any constant oxygen concentration (for example, $O_2=0\%$) and which receives the steady-state condition of $I_{o\ steady\ state}/I_{o\ steady\ state}$ was unity.

Figure 12:
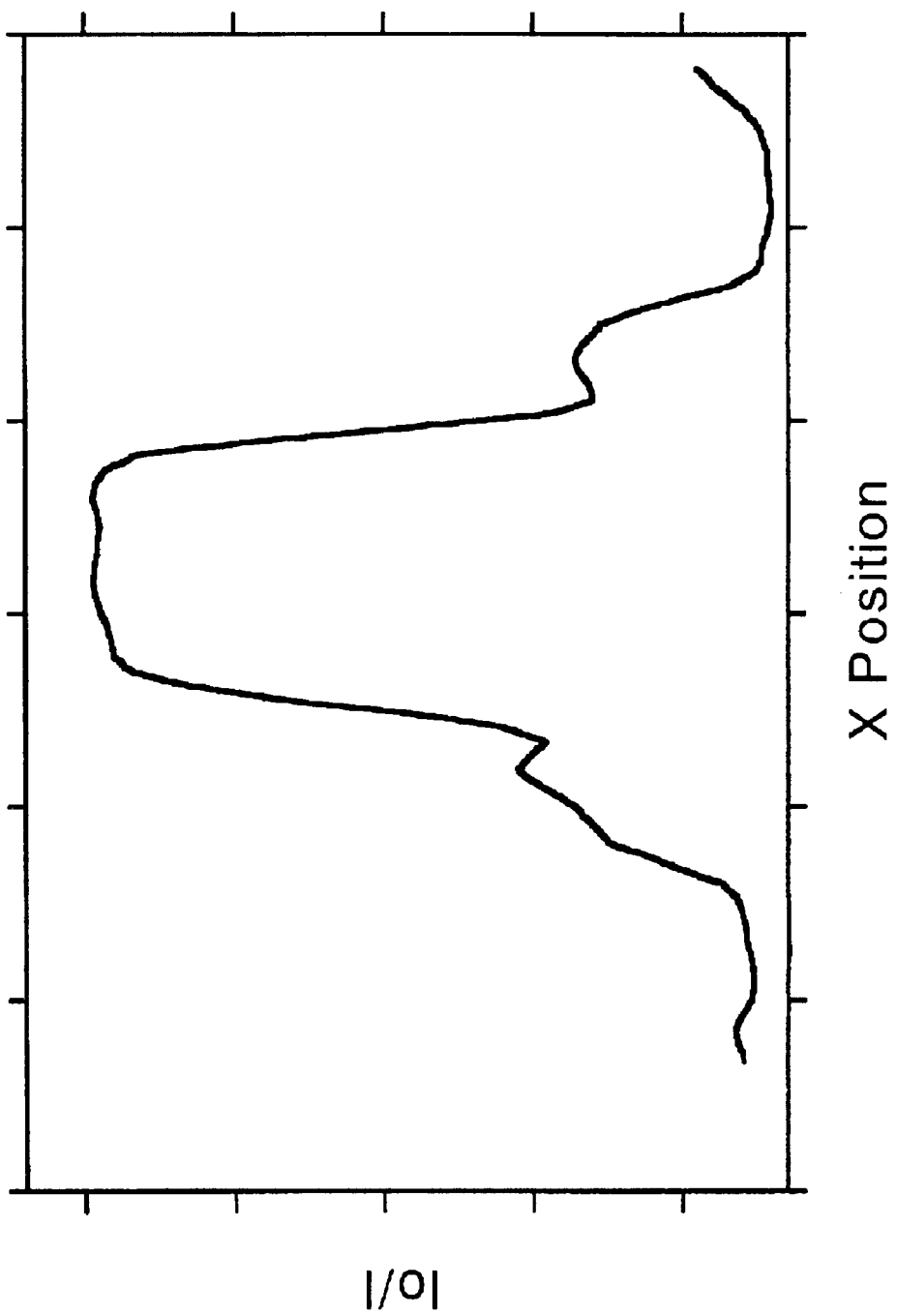
FIGS. 12–14 are graphs of time-resolved luminescence mapping of oxygen permeability of an array of coatings, with each graph representing a cross-section of three elements of the array after an exposure of 2 seconds, 30 seconds, and 4 minutes, respectively, of the array to oxygen.
Figure 13:
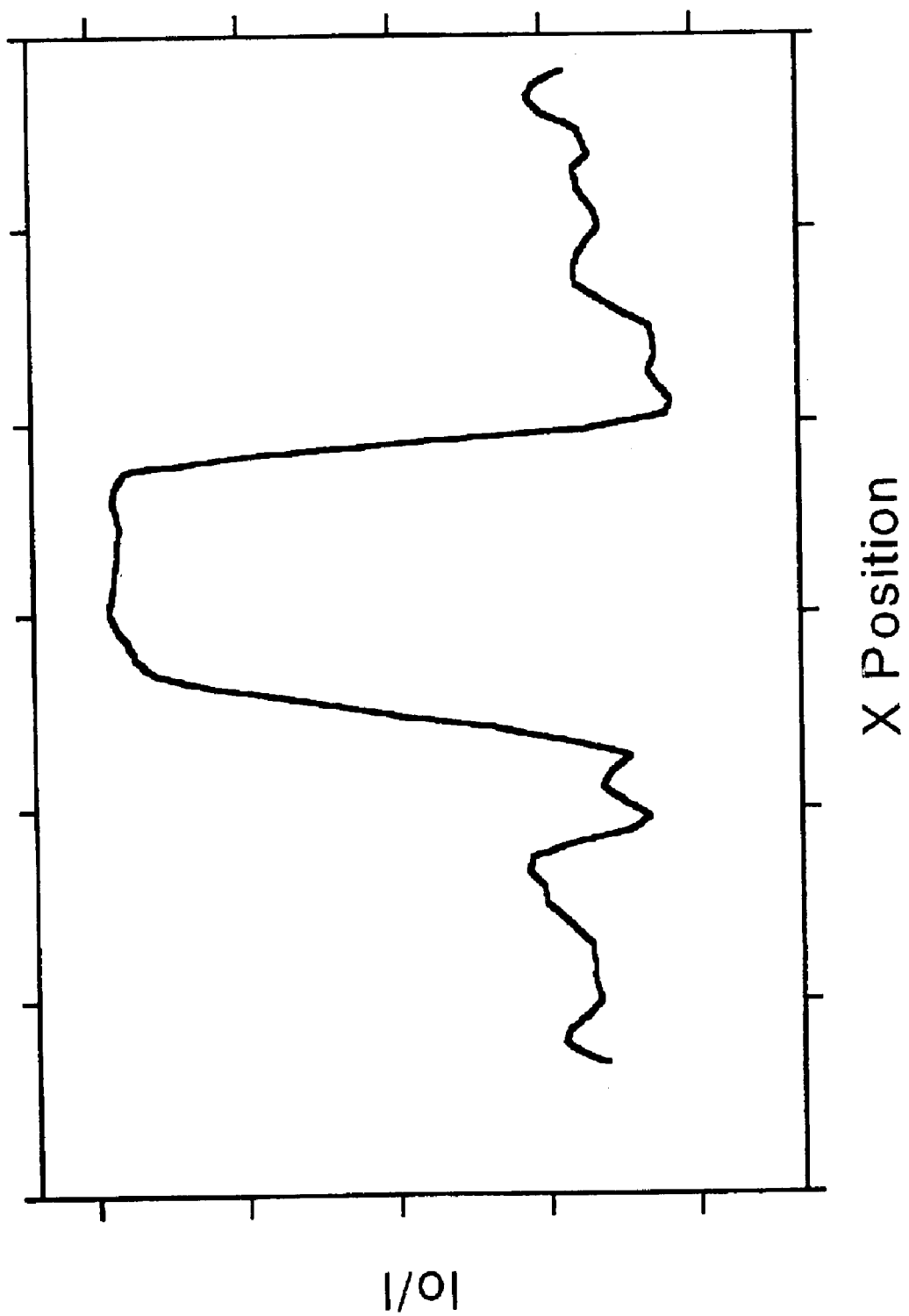
Figure 14:
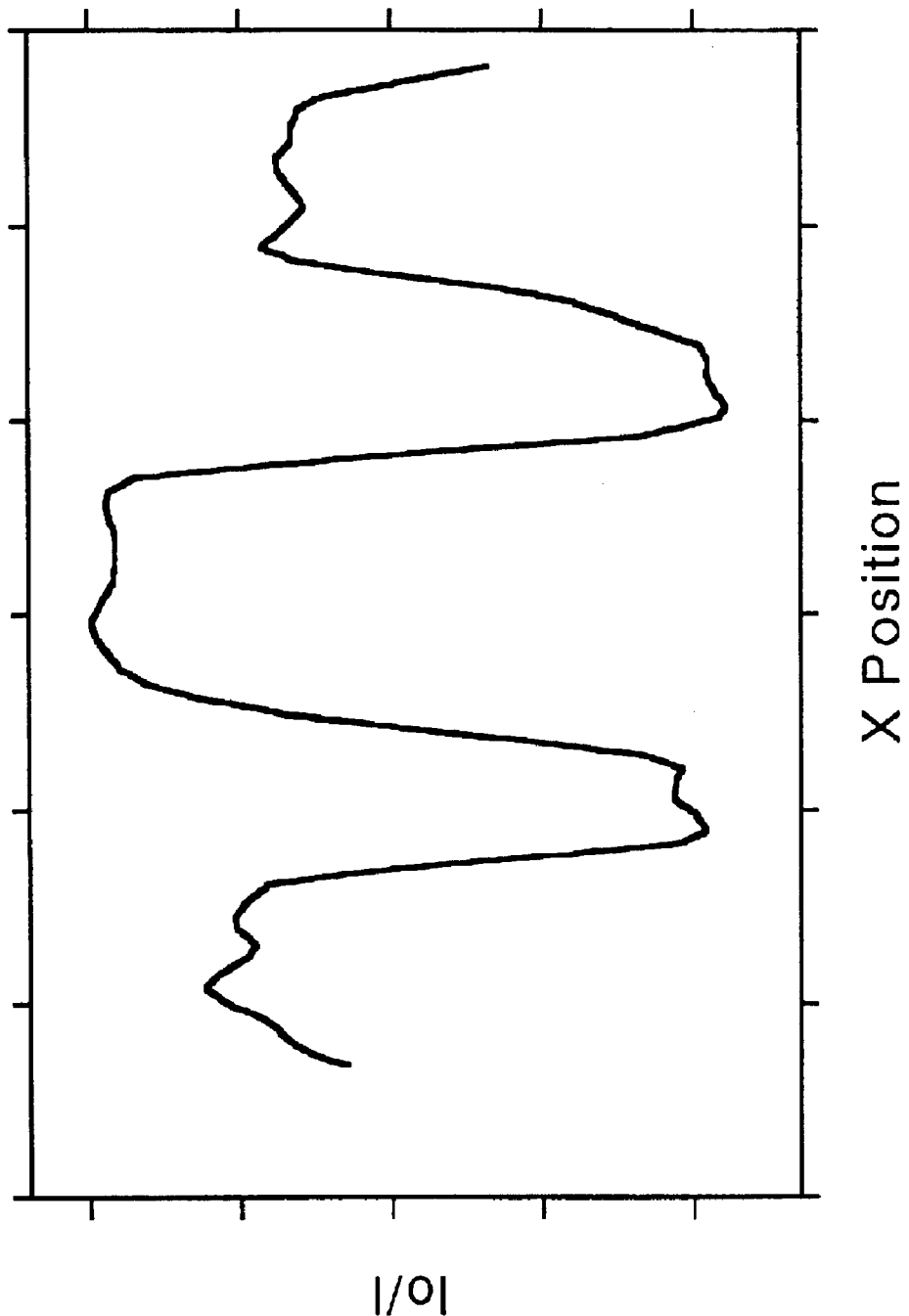

An experimental verification of the method for mapping of oxygen permeability in accordance with the present invention is presented in FIGS. 12–14. These figures present time-resolved luminescence mapping of oxygen permeability of arrays of coatings. Each plot is a cross section over three elements of the array and is a result of a ratio of an image of the array in a blank gas (nitrogen) over the image of the sensor after a given time delay after exposure to analyte gas (oxygen). FIG. 12 shows the cross section of the ratiometric image of three elements of the array after 2 seconds after exposure of the array to oxygen. FIG. 13 shows the same cross section after 30 seconds after exposure of the array to oxygen. FIG. 14 shows the same cross section after 4 minutes after exposure of the array to oxygen.

Another example includes evaluation of moisture sensitivity of reagent-doped polymeric materials. Different dyes were dissolved in polymer solutions in organic solvents. Film deposition was performed using about 20-microliter volumes of the film formulations and pipetting the formulations into 48 separate spatial locations on a 12×9-cm sheet of PET and evaporating the solvents from the film. The 48-element coating library contained eight different coating formulations with six replicates each. The coating formulations are provided in Table2.

TABLE 2

Coating Formulations for Serial Analysis

| Coating | Coating Reagent | Coating Description |
|---|---|---|
| 1 | malachite green | 1 mM reagent in 5% w/w solution of perfluorosulfonic acid-PTFE copolymer |
| 2 | methylene blue | 1 mM of reagent in 5% w/w solution of perfluorosulfonic acid-PTFE copolymer |
| 3 | crystal violet | 1 mM of reagent in 5% w/w solution of perfluorosulfonic acid-PTFE copolymer |
| 4 | prodan | 1 mM of reagent in 5% w/w solution of perfluorosulfonic acid-PTFE copolymer |
| 5 | rhodamine 6G | 1 mM of reagent in 5% w/w solution of perfluorosulfonic acid-PTFE copolymer |
| 6 | DCM | 1 mM of reagent in 5% w/w solution of perfluorosulfonic acid-PTFE copolymer |
| 7 | nile red | 1 mM of reagent in 5% w/w solution of perfluorosulfonic acid-PTFE copolymer |
| 8 | 7-hydroxycoumarin | 1 mM of reagent in 5% w/w solution of perfluorosulfonic acid-PTFE copolymer |

Figure 15:
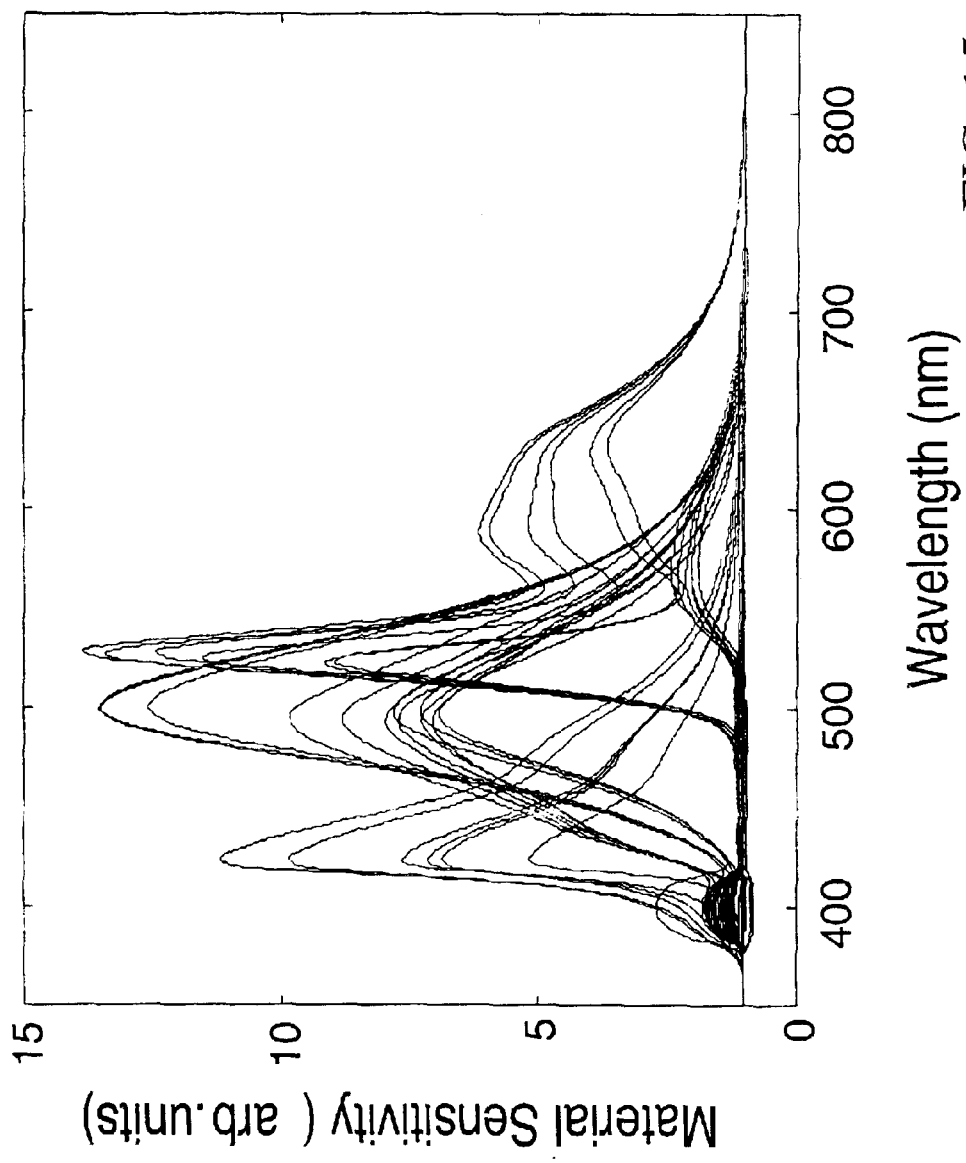
FIGS. 15 and 16 are graphs of an optical analysis comparing material sensitivity to wavelength associated with an array of coatings at an excitation wavelength of about 400 nm and 470 nm, respectively.
Figure 16:
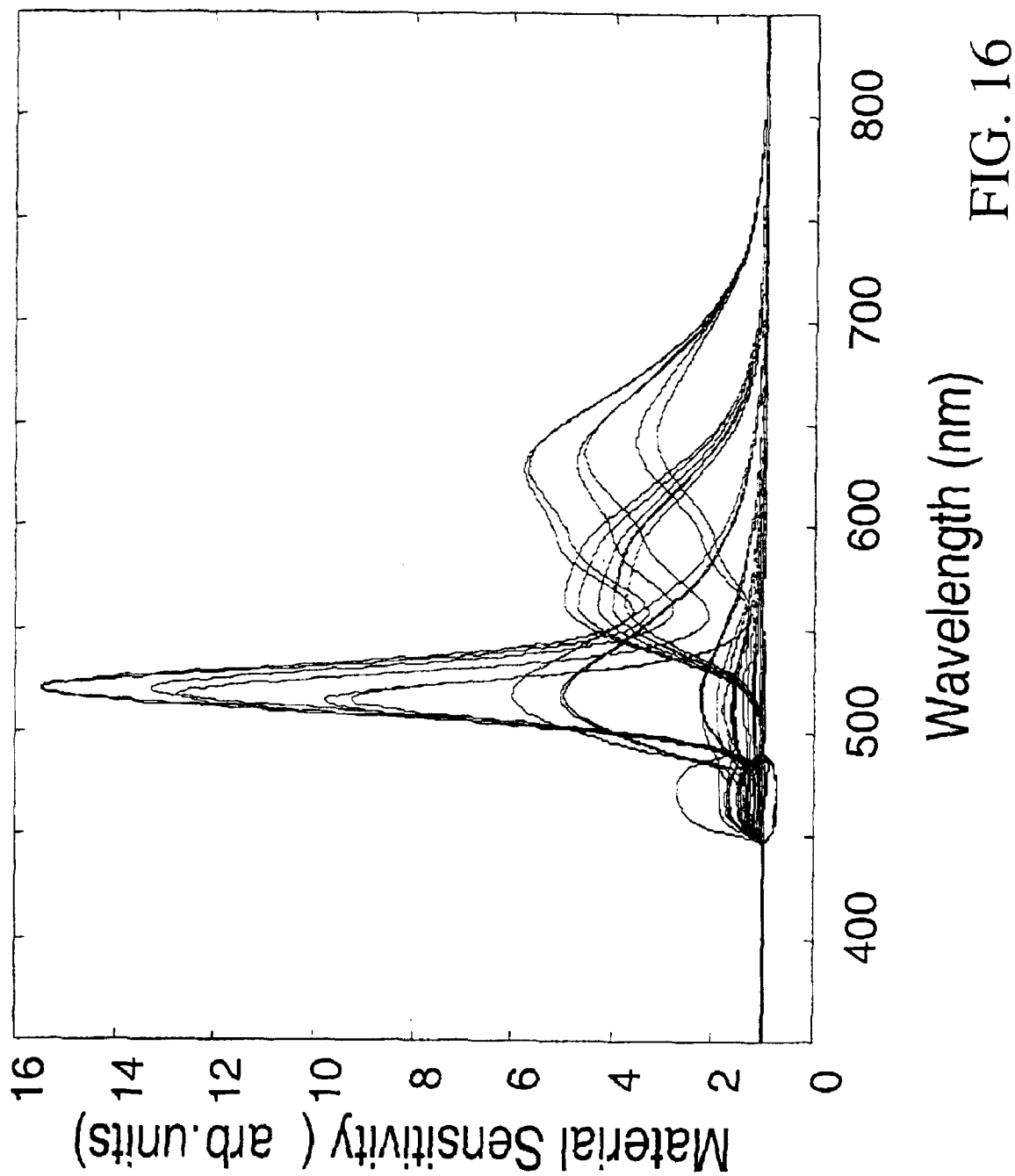

The coating library was analyzed before and after exposure of the coating array to moist air, with a relative humidity of about 80%. Luminescence measurements were performed on a setup which included a white light source (450-W Xe arc lamp, SLM Instruments, Inc., Urbana, Ill., Model FP-024), a monochromator for selection of the excitation wavelength (SLM Instruments, Inc., Model FP-092), and a portable spectrofluorometer (Ocean Optics, Inc., Dunedin, Fla., Model ST2000). The spectrofluorometer was equipped with a 200-$\mu$m slit, 600-grooves/mm grating blazed at 400 nm and covering the spectral range from 250 to 800 nm with efficiency greater than 30%, and a linear CCD-array detector. Excitation light from the monochromator was focused into one of the arms of a "six-around-one" bifurcated fiber-optic reflection probe (Ocean Optics, Inc., Model R400-7-UV/VIS). Emission light was collected from a sample when the common end of the fiber-optic probe was positioned near the sample at a certain angle to minimize the amount of excitation light reflected from the sample back into the probe. The second arm of the probe was coupled to the spectrofluorometer. The coating array was positioned in a flow-through cell with transparent windows for optical analysis of materials in the cell. The cell with the coating array was positioned on a automated XY translation stage. The results of the serial analysis of the coatings are presented in FIGS. 15 and 16, showing the relative sensitivity of the reagent-doped coatings to moisture at the excitation wavelength of about 400 nm, and about 470 nm, respectively.

Figure 17:
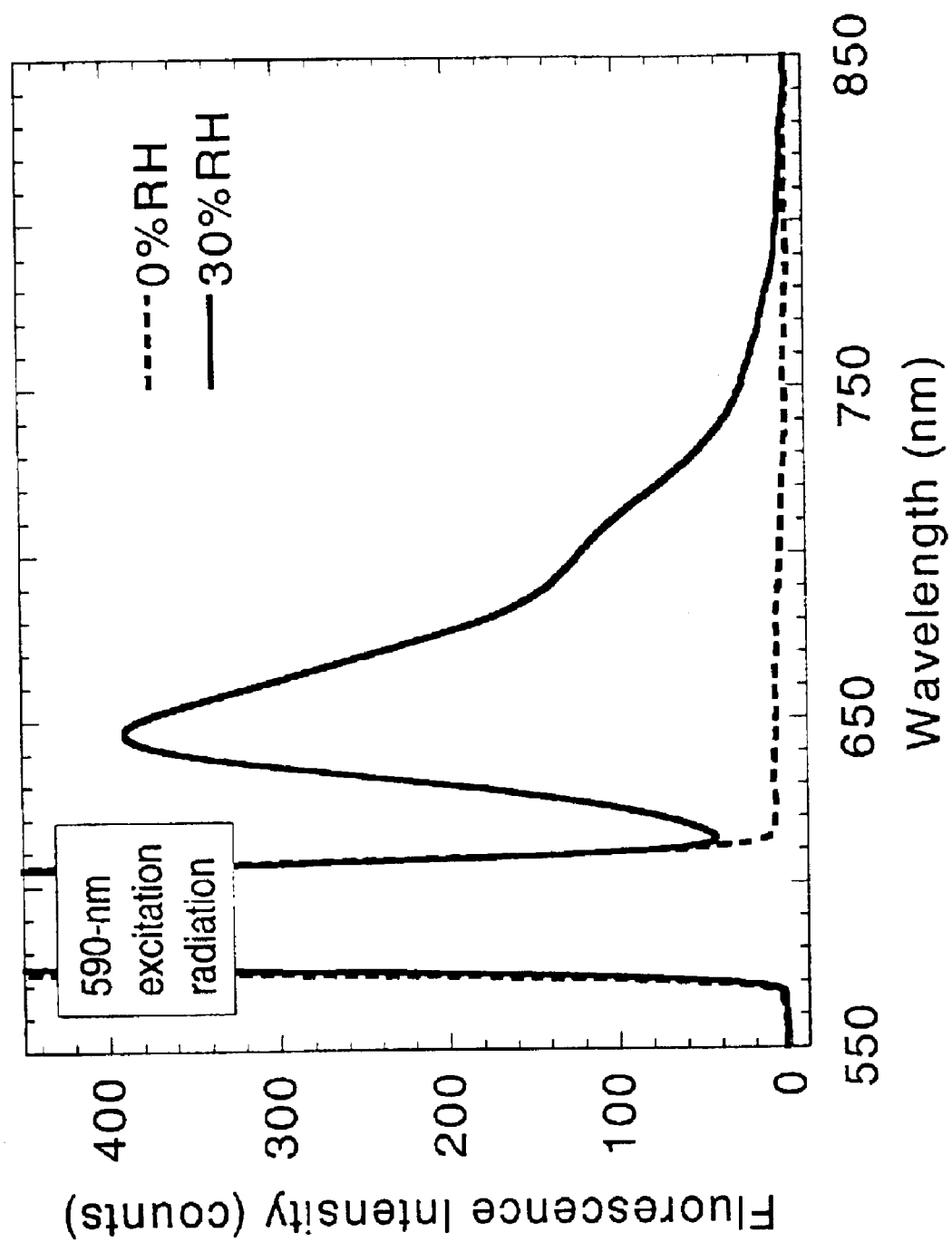
FIG. 17 is a graph of a dynamic response associated with one coating at a 590 nm excitation wavelength at about 0% and 30% relative humidity.

Referring to FIG. 17, further evaluation demonstrated that coating #7 provided an increase in luminescence signal upon exposure to moisture when a 590-nm radiation was used for excitation. In addition, the background of the emission in dry gas was low. FIG. 17 also demonstrates spectra of such materials in dry atmosphere and at 30% relative humidity.

Figure 18:
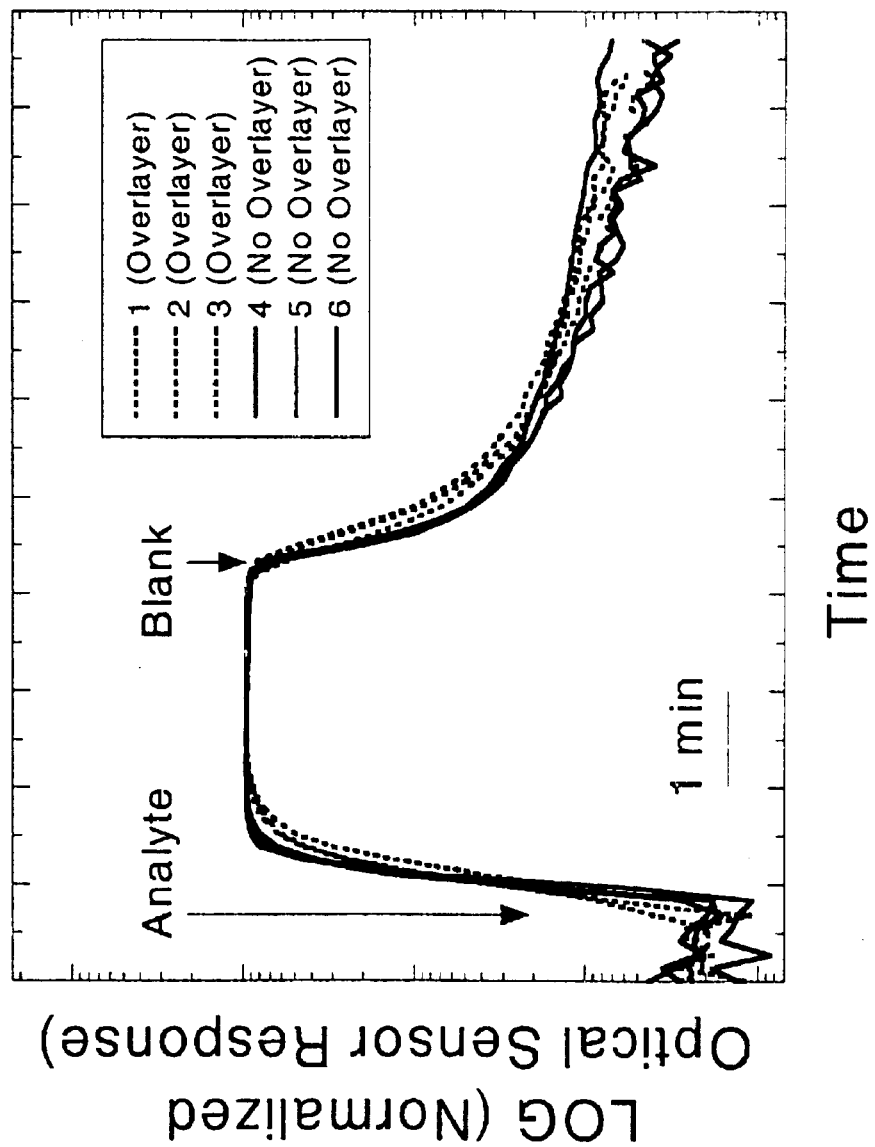
FIG. 18 is a graph comparing a dynamic response of three sensor regions with a protective overlayer and three sensor regions without a protective overlayer for an optical sensor.

Three replicates from each different coating formulation were coated with a solvent resistant protective overlayer. Comparison of dynamic response of sensor regions without and with the protective overlayer demonstrated that the overlayer does not significantly increase the response time of the sensor structure. A typical plot of the dynamic response of three sensor regions with the protective overlayer and three sensor regions without the protective overlayer, for example using coating #7, is presented in FIG. 18.

Another example includes the use of acoustic wave sensors. AT-cut quartz crystals with gold electrodes were used as thickness shear mode (TSM) transducers. These crystals oscillate in the thickness-shear mode with a fundamental frequency of about 10 MHz. The crystals were coated with a chemically sensitive polymeric material with a partition coefficient toward volatile solvents of about 500 100000. Several crystals were coated with a protective overlayer. Crystals with and without the overlayer were arranged in an array and exposed to different concentrations of solvent vapors. The resonant oscillation frequency of the array of transducers was monitored using 225-MHz Universal Counters (model HP 53132A, Hewlett Packard, Santa Clara, Calif.) as a function of time. Data acquisition was performed with a laptop PC using a program written in LabVIEW (National Instruments, Austin, Tex.).

Figure 19:
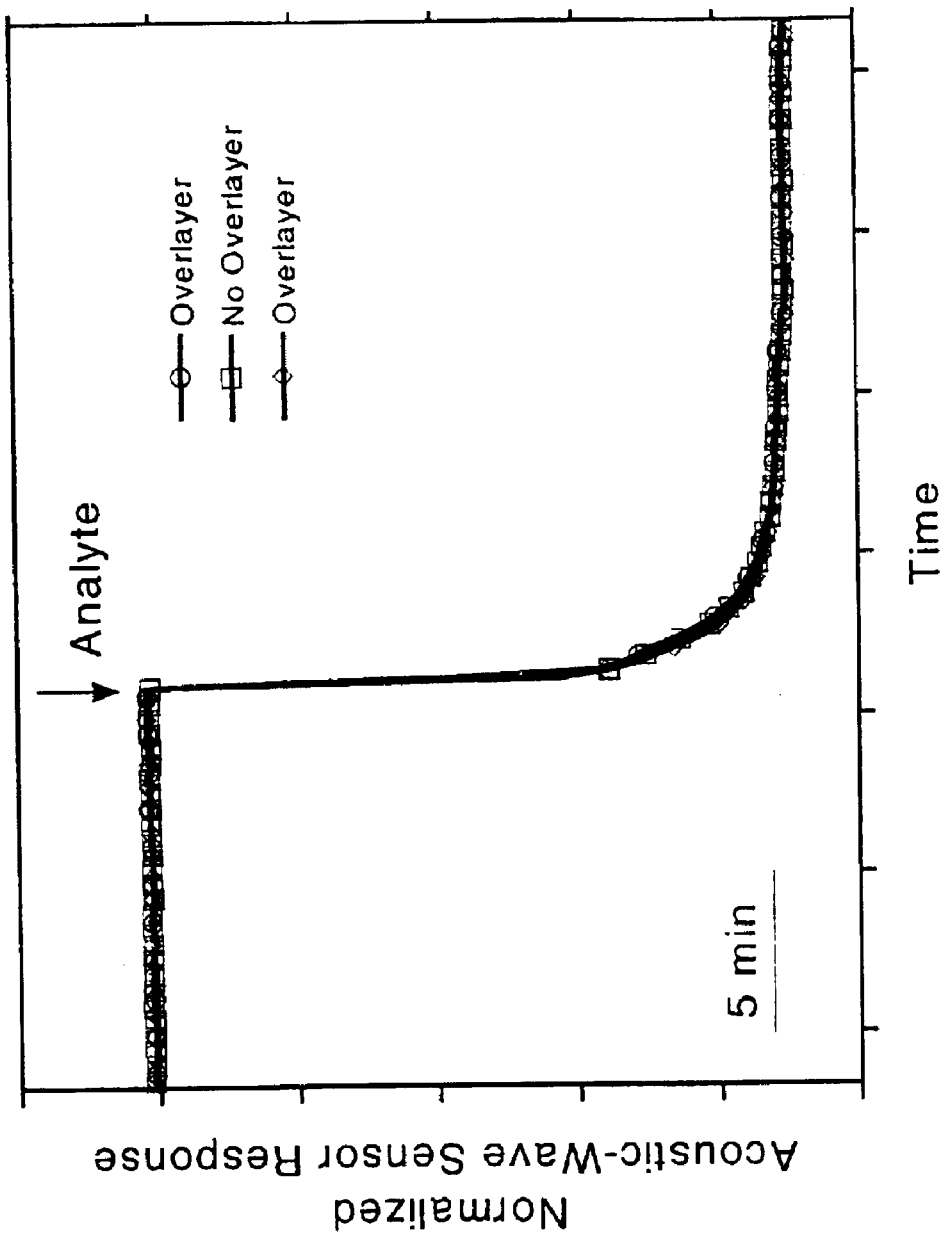
FIG. 19 is a graph comparing a dynamic response of sensor regions with and without a protective overlayer for an acoustic wave sensor upon introduction of a fluid of interest.
Figure 20:
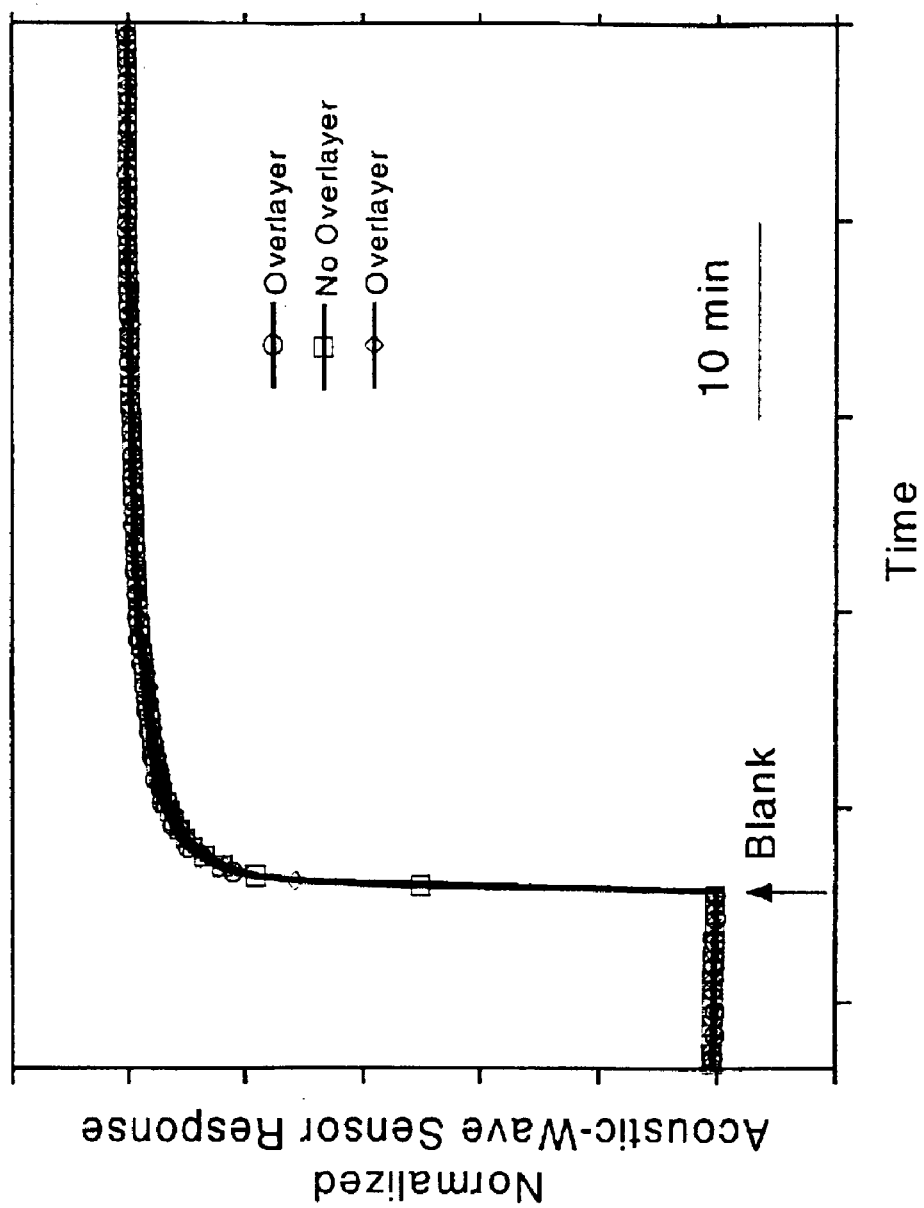
FIG. 20 is a graph comparing a dynamic response of the sensor regions of FIG. 19 upon the purging of the fluid of interest.

Comparison of dynamic response of sensors without and with the protective overlayer demonstrated that the overlayer does not significantly increase the response time of the sensor structure upon their exposure to vapors of organic solvents at concentrations of 10 100 ppm. A typical plot of the dynamic response of sensors with and without the protective overlayer upon introduction of 30 ppm toluene vapor is presented in FIG. 19. A typical plot of the dynamic response of sensors with and without the protective overlayer upon purging toluene vapor with a blank gas (nitrogen) is presented in FIG. 20.

It should be understood that protective overlay may be applied to any type of sensor to shield the sensing layer of the sensor from being affected by any chemical component of a barrier coating. For example, the protective overlay may be incorporated into optical sensors, acoustic wave sensors, chemical resistors, conductivity sensors, MEMS sensors, etc., in order to improve the accuracy of determining a measure of a barrier property of a given coating to a given analyte or fluid of interest. Therefore, not only may the optical properties of the sensor be determined, but other associated properties such a vibration frequency associated with a mass change, a chemical resistor value, a conductivity value, etc., may be measured and correlated to a barrier property metric for the associated coating.

Example embodiments of the present invention have now been described. It will be appreciated that these examples are merely illustrative of the invention. Many variations and modifications will be apparent to those skilled in the art.

What is claimed is:

1. A sensor device for determining a barrier property of a coating with respect to a fluid of interest, the sensor device comprising:
   a substrate;
   a sensing layer on the substrate comprising a material having a predetermined response to an exposure to the fluid of interest;
   a protective overlayer that covers the sensing layer, wherein the protective overlayer comprises a chemically-resistant and a solvent-resistant material that allows for the transport of the fluid to the sensing layer; and
   an array of barrier coatings having spatial variations of permeability across the array of barrier coatings.

2. The sensor device of claim 1, wherein the overlayer further comprises an amorphous fluoropolymer.

3. The sensor device of claim 1, wherein the overlayer further comprises a random copolymer of tetrafluoroethylene (TEF) and perfluoro-2,2-dimethyl-1,3-dioxole (PDD).

4. The sensor device of claim 1, wherein the overlayer further comprises a polyimide.

5. The sensor device of claim 2, wherein the sensing layer comprises a polymer.

6. The sensor device of claim 2, wherein the sensing layer comprises a sol-gel.

7. The sensor device of claim 2, wherein the sensing layer comprises a polymer and a luminophore.

8. The sensor device of claim 2, wherein the sensing layer comprises a polymer and a colorimetric reagent.

9. The sensor device of claim 2, wherein the sensing layer comprises a sol-gel and a colorimetric reagent.

10. The sensor device of claim 1, wherein a value of the predetermined response relates to a measurement of the barrier property.

11. A system for determining a barrier property of an array of barrier coatings with respect to a fluid of interest, comprising:
   a sensor device on which the array of barrier coatings are disposed, the sensor device having a substrate, a sensing layer and a protective overlayer that covers the sensing layer, where onto the protective layer are applied the array of barrier coatings, the sensing layer comprising a material having a predetermined response to an exposure to the material of interest, the overlayer comprising a chemically-resistant and a solvent-resistant material that allows for the transport of the fluid to the sensing layer;
   a radiation source having an output for generating a reference radiation directable toward the sensor device, wherein an interaction between the reference radiation and the sensor device generates a resultant radiation; and
   a detector for measuring characteristics of the resultant radiation, wherein the measured characteristics of the resultant radiation are relatable to a barrier property for each of the array of barrier coatings.

12. The system of claim 11, wherein the overlayer further comprises an amorphous fluoropolymer.

13. The system of claim 11, wherein the overlayer further comprises a random copolymer of tetrafluoroethylene (TEF) and perfluoro-2,2-dimethyl-1,3-dioxole (PDD).

14. The system of claim 12, wherein the sensing layer comprises a polymer.

15. The system of claim 12, wherein the sensing layer comprises a polymer and a fluorophore.

16. A device for mapping of barrier coatings, the device comprising:
   a sensor with a substrate having at least one external surface;
   a sensing layer on the substrate
   a protective overlayer that covers the sensing layer, wherein the protective overlayer is applied to at least one external surface, wherein the protective overlayer comprises a chemically-resistant and a solvent-resistant material that allows for the transport of a fluid of interest to the sensor;
   an array of barrier coatings in a library deposited onto the protective overlayer; and
   a measurement device for measuring variation in analytical signal for the array of barrier coatings exposed to the fluid of interest.

17. The device of claim 16, wherein the sensor comprises a fluid-permeable substrate or a fluid-impermeable substrate.

18. The device of claim 16, wherein the sensor is selected from the group consisting of an optical sensor, an acoustic wave sensor, a chemical resistor, a micro-electro-mechanical system sensor, and an electrochemical sensor.

19. The device of claim 16, wherein the sensor is an optical sensor selected from the group consisting of a colorimetric sensor, a luminescent sensor, a chemiluminescent sensor, a vacuum UV absorbance sensor, a UV-vis absorbance sensor, an infrared absorbance sensor, a Raman sensor, an interferometric sensor, a polarization sensor, and a luminescence lifetime sensor.

20. The device of claim 16, wherein the fluid of interest is selected from the group consisting of water vapor and oxygen.

21. The device of claim 16, wherein the variation in analytical signal comprises a variation in luminescence that varies with permeability of barrier coatings in the array of barrier coatings to the material of interest.

22. The device of claim 17, wherein the sensor comprises an array of sensor regions.

23. The device of claim 17, wherein the sensor comprises an oxygen sensor.

24. The device of claim 16, wherein the fluid of interest is oxygen.

25. The device of claim 16, wherein the sensor comprises a luminophore.

26. The device of claim 16, wherein the variation in analytical signal comprises a variation in luminescence measured over time.

27. The device of claim 16, wherein the variation in analytical signal comprises a variation in luminescence intensity.

28. The device of claim 16, wherein the variation in analytical signal comprises a variation in luminescence lifetime.

29. The device of claim 16, wherein the measurement device comprises a multichannel detector.

30. A method for measuring barrier properties of barrier coatings, the method comprising:

providing a chemical sensor having at least one external surface;

applying to a substrate a sensing layer to at least one external surface;

applying a protective overlayer that covers the sensing layer to the at least one external surface of the chemical sensor, the protective overlayer comprising a chemically-resistant and a solvent-resistant material that allows for the transport of a fluid of interest to the sensing layer;

placing an array of barrier coatings on the protective overlayer;

exposing the array of barrier coatings to the fluid of interest; and measuring a variation in the barrier properties of the array of barrier coatings.

31. The method of claim 30, where the array of barrier coatings includes reference regions such that a relative performance of each of the array of barrier coatings may be determined.

32. The method of claim 31, where the sensor comprises a luminescent sensor.

33. The method of claim 32, where measuring a variation in the barrier properties comprises measuring a variation in luminescence of each of the array of barrier coatings.

34. The method of claim 33, further comprising comparing a luminescence signal for a chemically sensitive layer beneath the array of barrier coatings for regions having barrier coatings to a luminescence signal produced by the reference regions.

35. The method of claim 34, wherein the reference regions comprise a portion of the sensor having no barrier coating applied or having a coating with known characteristics.

36. The method of claim 30, where variation in barrier properties comprises measuring variation in luminescence of the array of barrier coatings via obtaining a digital photograph of the array of barrier coatings.

* * * * *